(12) United States Patent
Meynink et al.

(10) Patent No.: US 9,259,547 B2
(45) Date of Patent: Feb. 16, 2016

(54) SYSTEMS FOR REDUCING EXHALATION PRESSURE IN A MASK SYSTEM

(75) Inventors: Sofietje Meynink, Turramurra (AU);
Bruce Richard Davies, Strathfield (AU);
James Morrison, Thornleigh (AU);
Robert Edward Henry, Roseville (AU);
Lee James Veliss, West Ryde (AU)

(73) Assignee: RedMed Limited, Bella Vista (AU)

(*) Notice: Subject to any disclaimer, the term of this patent is extended or adjusted under 35 U.S.C. 154(b) by 2110 days.

(21) Appl. No.: 12/438,871

(22) PCT Filed: Sep. 6, 2007

(86) PCT No.: PCT/AU2007/001301
§ 371 (c)(1),
(2), (4) Date: Oct. 21, 2009

(87) PCT Pub. No.: WO2008/028228
PCT Pub. Date: Mar. 13, 2008

(65) Prior Publication Data
US 2010/0043796 A1    Feb. 25, 2010

(30) Foreign Application Priority Data

Sep. 7, 2006    (AU) ................................ 2006904898
Oct. 26, 2006   (AU) ................................ 2006905948
Oct. 27, 2006   (AU) ................................ 2006905404

(51) Int. Cl.
*A61M 11/00*    (2006.01)
*A61M 16/06*    (2006.01)
*A61M 16/20*    (2006.01)

(52) U.S. Cl.
CPC ............... *A61M 16/06* (2013.01); *A61M 16/20* (2013.01)

(58) Field of Classification Search
CPC ............................. A61M 16/06; A61M 16/20
USPC ............. 128/205.24, 204.18, 204.26, 207.12, 128/206.12, 912, 206.21, 205.11
See application file for complete search history.

(56) References Cited

U.S. PATENT DOCUMENTS

| | | | |
|---|---|---|---|
| 4,821,713 A | | 4/1989 | Bauman |
| 4,823,828 A | | 4/1989 | McGinnis |
| 5,549,106 A | * | 8/1996 | Gruenke et al. ......... 128/204.23 |
| 5,685,296 A | * | 11/1997 | Zdrojkowski et al. ... 128/205.24 |
| 5,765,553 A | * | 6/1998 | Richards et al. ......... 128/203.29 |
| 5,988,160 A | * | 11/1999 | Foley et al. ............. 128/200.22 |
| 6,006,748 A | * | 12/1999 | Hollis ...................... 128/205.24 |
| 6,080,461 A | | 6/2000 | Wozniak et al. |
| 6,102,038 A | | 8/2000 | DeVries |
| 6,189,532 B1 | * | 2/2001 | Hely et al. ............... 128/205.24 |
| 6,192,876 B1 | * | 2/2001 | Denyer et al. ............ 128/205.25 |
| 6,253,764 B1 | * | 7/2001 | Calluaud ................. 128/204.18 |
| 6,581,601 B2 | | 6/2003 | Ziaee |

(Continued)

OTHER PUBLICATIONS

International Search Report mailed Jan. 21, 2008 in PCT/AU2007/001301.

*Primary Examiner* — Steven Douglas
(74) *Attorney, Agent, or Firm* — Nixon & Vanderhye P.C.

(57) ABSTRACT

An apparatus for improving patient comfort during CPAP therapy includes a venting arrangement arranged to reduce expiratory pressure. A mask system for providing CPAP therapy to a patient includes a mask; a flow generator to provide a flow of pressurized breathable gas; a tube to connect the mask to the flow generator; and a venting arrangement arranged to reduce expiratory pressure.

43 Claims, 29 Drawing Sheets

(56) References Cited

U.S. PATENT DOCUMENTS

| | | | |
|---|---|---|---|
| 6,629,529 B2 * | 10/2003 | Arnott | 128/204.23 |
| 6,851,425 B2 * | 2/2005 | Jaffre et al. | 128/204.18 |
| 7,036,506 B2 | 5/2006 | McAuliffe et al. | |
| 7,901,361 B2 * | 3/2011 | Rapoport et al. | 600/533 |
| 2004/0094157 A1 | 5/2004 | Dantanarayana et al. | |
| 2004/0246649 A1 | 12/2004 | Besen | |

* cited by examiner

1. CPAP

2. APAP (auto-CPAP), e.g. Resmed's autoSet

3. Bi-level, e.g. ResMed's VPAP

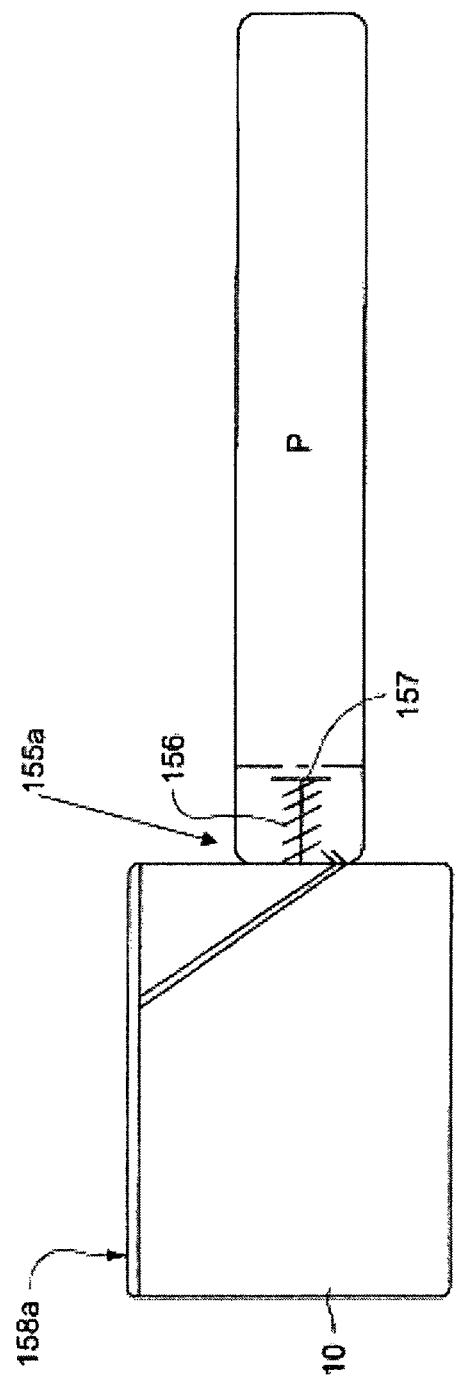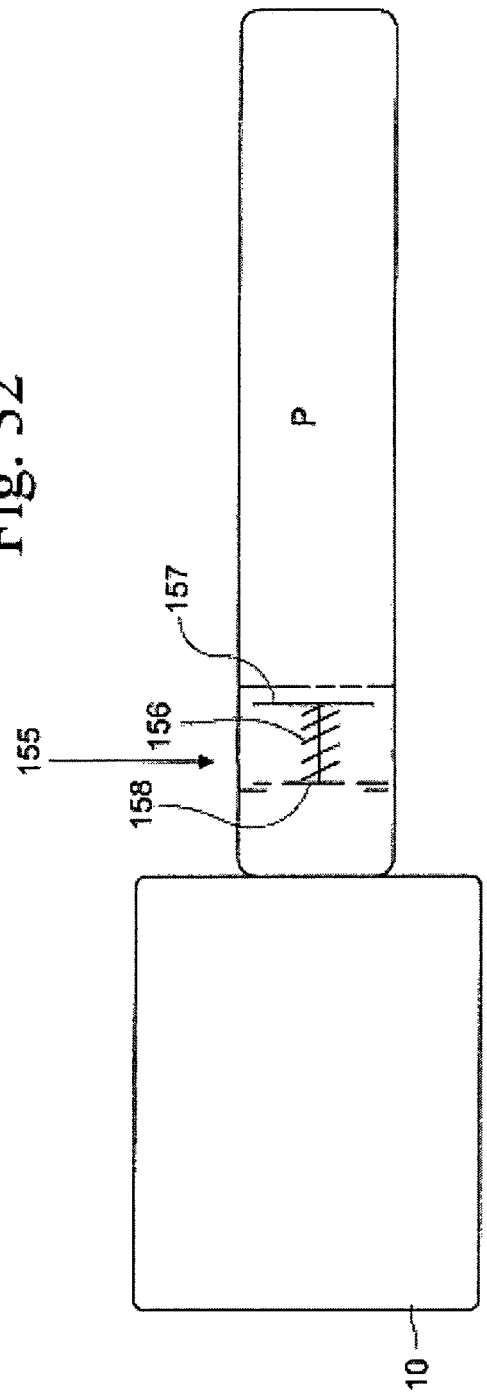

SYSTEMS FOR REDUCING EXHALATION PRESSURE IN A MASK SYSTEM

CROSS REFERENCE TO RELATED APPLICATIONS

This application is the U.S. national phase of International Application No. PCT/AU2007/001301, filed Sep. 6, 2007, which designated the U.S. and claims priority to Australian Provisional Applications 2006904898, 2006905948 and 2006906404 filed Sep. 7, 2006, Oct. 26, 2006, and Oct. 27, 2006, respectively, the entire contents of each of which are hereby incorporated by reference.

FIELD OF THE INVENTION

The present invention relates to systems and methods for reducing exhalation pressure in a mask system used to deliver a pressurized flow of breathable gas to a patient.

BACKGROUND OF THE INVENTION

Obstructive sleep apnoea (OSA) is a sleep breathing disorder where the upper airway collapses during sleep. Most patients diagnosed with OSA are treated with continuous positive airway pressure (CPAP), which acts as an air splint to hold the upper airway open. This is delivered to the patient with a flow generator and mask system while they sleep.

Although CPAP provides effective therapy, compliance rates are suboptimal. The constant pressure provided feels unnatural and many patients have difficulty breathing out against the pressure. This reduces the patient tidal volume. Current vented masks can have a high airflow causing excess noise, airflow and high power requirements. The current solutions are complex and relatively expensive, involving a special flow generator that reduces the pressure on exhalation (e.g. Bi Level Flow Generator).

Most patients on CPAP are older. While some can afford expensive therapy many of these people are on pensions or Social Security and have limited spending money for therapy. Patients that are predisposed to not accept therapy are less likely to want to spend more money to get additional features, even if they are aimed at improving compliance. Patients may not be able to afford the high level technology and may miss out on therapy altogether.

A low level technological product would be the most effective solution as it has the lowest costs involved, but has the potential to make a significant difference. There are currently no lower technology solutions for flow or pressure reduction or modification that the patient can use on their current CPAP flow generator.

There are a few inexpensive accessories available to OSA patients on CPAP. Chinstraps can be used to minimise mouth leak that causes the upper airway to dry out making the patient uncomfortable. Chinstraps are available for around thirty dollars or less. Other solutions such as nasal sprays and earplugs can also help.

If the patient has adequate and appropriate support and education, there are only two modifications to CPAP therapy that have been shown to improve compliance. These are humidification and pressure reduction. These are regarded as high-tech solutions.

There are a variety of devices that reduce the average treatment pressure delivered to the patient. Some examples include variable pressure devices, bi-level devices, expiratory pressure relief devices and ventilators. FIGS. 1A, 1B and 1C show the basic differences between how these devices can change or maintain flow with time. Although not depicted, these devices can also change or maintain pressure differently over time. The changes can occur on different time scales.

There is currently no low-level technology that has the potential to control pressure and flow on a breath-by-breath basis to improve breathing comfort on CPAP. Although other valves and devices have been investigated as potential solutions, nothing was found that solves the problems in a manner as satisfactory as the present invention.

Pressure Regulator Devices

Referring to FIG. 2, one device currently available is the SoftX™ from Invacare Corporation. The SoftX™ is provided with the Polaris EX™ CPAP device from Invacare. The SoftX™ is not a true example of a low-technology device as it bridges the gap between a high-level technology device and a low level device. It uses a combination of electronics and a mechanical solution by using a pressure transducer to sense the pressure and open a valve to divert the flow.

The SoftX™ device does not provide pressure relief, only pressure swing reductions, as shown in FIG. 3. Additionally, the SoftX™ device does not reduce the pressure spike, only the duration of the spike. There is no evidence that pressure swing reductions is enough to improve compliance significantly. In fact, there is very little information on the effect of pressure swing reductions on compliance.

Another example of a pressure regulating device is disclosed in U.S. Pat. No. 7,036,506, to the Assignee of the instant application. This patent describes a device to control the pressure or flow rate of the air supplied to a patient during CPAP with reduced noise, flow fluctuations and response time. The flow is never restricted beyond a point regardless of the position of the vane. This device is useful as previous devices choked the flow making the motor stall and slow to start again. When the patient exhales the flow is stopped and so flow to and from the blower stops, choking the motor. This means there is a delay in the response time of the CPAP machine from exhalation to inhalation. This involves a vane that directs most of the air from the inlet port to either the exhaust port or the outlet port or fraction of air to each. The vane can be angularly rotated to change the direction of the air to the various ports. Again, this valve in not true pressure relief, as it controls and regulates the flow.

Positive End-Expiratory Pressure (PEEP) Valves

Positive End-Expiratory Pressure (PEEP) valves control positive and expiratory pressure in conjunction with a medical respiration apparatus. This is so the patient has a set preset maximum positive end expiration pressure. The valve is controlled by a spring that is biased toward a closed position to prevent exhalation flow until the threshold resistance is overcome. A soft spring is used to preload a valve disk, which covers a port that is exposed to the controlled pressure. The tension of the spring is used to adjust the valve threshold pressure over a range that is useful for a clinical application of 4 to 20 cm $H_2O$. There have been some problems with PEEP valves as the preload deformation of the spring has to be relatively large to achieve the clinical range of pressures.

PEEP valves are suitable for use with resuscitators, ventilators and CPAP systems. The expiratory connection must be airtight so that positive pressure can be achieved during the expiratory phase. PEEP valves do not influence the inspiratory $O_2$ concentration or the inspiratory resistance of the patient. This means that the PEEP valve is suitable for spontaneous breathing and resuscitation and can remain at the patient valve at all times.

PEEP valves simply regulate the pressure in a mask. They do not relieve the pressure below the treatment pressure during expiration. The minimum pressure the valves allow in the mask is treatment pressure, as they regulate the pressure in such a way that there are instantaneous adjustments so that the pressure in the mask is stable. PEEP valves also represent a very simple, basic pressure regulation solution. The main disadvantages are that they are loud and waste treatment pressure and humidified air. They are also large and not aesthetically pleasing.

One example of a PEEP valve for use in conjunction with a medical respiration apparatus is shown in U.S. Pat. No. 4,823,828. The PEEP valve includes an adjustable spring for establishing and maintaining the threshold pressure of exhalation. It also has a flow control valve in which the disk structure uses the dynamic pressure of the exhalation flow to assist in providing control over, and fine adjustability of, the valve disk motion. This allows the continuous supply of flow during both the inhalation and exhalation phases of the breathing cycle. The PEEP valve simply regulates the pressure and flow to provide constant pressure. U.S. Pat. No. 4,823,828 refers to the PEEP valve as a "relief" valve because it relives peaks in pressure. However, the "relief" valve of U.S. Pat. No. 4,823,828 does not drop the pressure below a treatment pressure.

Demand Valves

A demand valve is used in scuba diving equipment to supply the diver with a breath of air at normal atmospheric pressure while they are deep underwater. The valve is fed from a low-pressure hose from a chamber called the first-stage. The demand valve is also known as second stage. When the diver breathes out, the air goes from the dry side of the diaphragm and is released to the outside through one-way valves. It also has a purge button that the diver can press to depress the diaphragm to make gas flow to blow water out of the mouthpiece. The basic mechanism is illustrated in FIG. 4.

The valve is dependent on the person's breathing work and so is only triggered when the person initiates a breath. Lower breathing work means a lower effort is required to breathe so it is more comfortable and natural to breathe. The system stores gas in a chamber. This chamber is connected to a mouthpiece or a full-face mask for the diver to breathe from. One side of the chamber is a flexible diaphragm.

The valve defaults to a closed position by a spring force activated by the downstream air pressure, which is labeled A in FIG. 5. This force is just enough to overcome the difference in pressure between the downstream air and the upstream balance chamber in a scuba system. The valve detects when the diver starts to inhale. This triggers the device to open a chamber to release the gas. The diver must overcome the spring force to open the valve. Breathing in lowers the pressure inside the chamber so that the diaphragm moves to release a lever, which opens the valve. The downstream air travels through a hole leading to the balance chamber and applies an upstream force slightly less than the downstream force allowing it to open. This is labelled B in FIG. 5.

The diver then finishes inhalation and starts to exhale. Upon exhalation the pressure inside the chamber increases and the diaphragm returns to its normal position and the valve closes.

Some passive semi-closed circuit re-breathers use a form of demand valve, which senses the volume of the loop and injects more gas when the volume falls below a certain level.

Scuba demand valves are designed to work at a range of pressures that occur as the diver descends to different depths. The valve of FIG. 5 is pneumatically balanced to maintain a preferred breathing resistance throughout the dive. As the ambient water pressure reduces on accent the resistance has to increase to prevent free flow.

These systems have two elements of adjustability. The demand valve allows the diver to adjust inhalation effort as the conditions change. Also, an adjustable deflector vane diverts airflow from the valve directly into the mouthpiece for added comfort. This results in a smooth assisted inhalation that is fully adjustable.

A scuba valve system such as that shown in FIG. 5 could not be applied to a CPAP system without modification. One reason is that the driving pressures are a lot higher in the scuba mechanism, so triggering does not have to be as sensitively balanced. The pressure is stored in a container in a scuba demand valve so two stages are necessary: a pressure reduction device (discussed in more detail below) and the demand valve. In a CPAP application, this is more complex as the pressure is not stored. The valve must work on both a flow generator with pressure feedback and also a straight flow generator.

Additionally, there must not be a situation where a vacuum is introduced at the patient interface. The patient must be receiving treatment pressure at all times during inspiration and should receive a baseline pressure during expiration. This complicates triggering and the device.

In a patient device, there must also not be a purge function. This means that the diaphragm cannot be placed between the airway pressure and atmospheric pressure (in the case of scuba—water pressure). The consequence of this is that the operation of the closing spring and the diaphragm cannot remain the same as in the scuba valve, and that the placement of the diaphragm must be within the mask system.

The demand valves in ventilators are designed to meet the varying principles of the emergency medical services and rescue personal. It works according to the same principles as a scuba demand valve. This system also has a pressure relief system. The manual ventilation flow rate is fixed at 40 L/m, which meets the guidelines for resuscitation outlined by the American Heart Association. A demand valve resuscitator may be designed to provide 100% oxygen to a breathing patient, with minimal respiratory effort. It is designed to operate with flow rates up to 160 L/m and on one pressure of 50 psi or 344.7 kPa on an oxygen source. The valve also provides pressure relief for over 60 cm $H_2O$. In many current ventilators, the scuba-type actual demand valve is no longer provided. In some ventilators, the scuba-type demand valve is provided for the patient as a backup in case the machine shuts down.

While demand valves have not been applied to CPAP, they have been used in ventilators. There is no demand valve applied to CPAP applications for comfort. The demand valves used in ventilation use bottled oxygen under pressure, like a scuba demand valve. The pressures that are used are much higher than a CPAP application where the maximum pressure is generally 20 cm $H_2O$, making triggering easier. Application of demand valves to CPAP devices would involve many design challenges like triggering, comfort, flow generator compatibility, vent flow rate etc.

Solenoid Valves

A solenoid valve is a type of transducer device that converts energy into linear momentum. The valve is an integrated device that contains an electromechanical component that actuates either a valve, pneumatic or hydraulic, or a switch, which is a type of relay. Solenoid valves are usually used to control gases or fluids by shutting off, releasing, dosing, distributing or mixing. The benefits of these valves include that they are fast and safe to switch, have high reliability, a long service life, good compatibility of materials, low control power and are compact. The valves work by a mechanical switch that is activated by a magnetic coil. A solenoid valve may also be used to open and close an electric circuit, open or close a valve in a fluid pipe, or cause some mechanical action to be triggered. These by themselves could not be used to regulate the pressure, but they could help activate the device. They could also assist with minimising the cracking or activation pressure of a device.

U.S. Patent Application Publication 2004/0246649 A1 discloses a flow control valve with a magnetic field sensor. The valve is a solenoid device with a magnetic field sensor. The solenoid device includes a magnetic field generator that generates a magnetic flux that extends through a magnetic flux circuit member, formed at least in part from a ferromagnetic material and defining a gap that is effectively free of any ferromagnetic material. A magnetic flux sensor is disposed to sense a portion of the magnetic flux that extends across the gap. The solenoid device is disclosed as being implemented as a fluid flow control valve, and is not applicable to pressure relief as it would not relieve pressure on its own.

Pressure Regulation Valves

Referring to FIG. 6, a pressure regulation valve regulates the pressure using a sensing orifice. It is a large device used in industry with a similar concept as a PEEP valve. A pressure regulation valve may be preferred over a PEEP valve, as it does not blow off the pressure. However, the construction of a pressure regulation valve is more complicated than a PEEP valve. Pressure regulation valves are also used in a stage one regulator of a scuba system. However, the pressure regulation valve only regulates the duration of the pressure spike, but does not reduce the size of the pressure spike as discussed above.

One example of a flow regulation vent, or valve, for regulating flow from a pressurized gas supply is disclosed in U.S. Patent Application Publication 2004/0094157 A1, by the Assignee of the instant application. The pressure regulation valve is designed to lower $CO_2$ re-breathing in the mask, but also could be used as a one-way valve and an anti-asphyxia valve. The valve controls vent flow to give relatively high vent flow during low pressures and low vent flow during high pressures. The valve relies on flow rate to trigger it. As the patient breathes in, the flow to the mask increases and the flap on the valve blocks the vent.

The pressure regulation valve of U.S. Patent Application Publication 2004/0094157 A1 could be applied for the purpose of expiratory pressure relief to improve comfort, as when the patient breathes out the flow to the mask decreases and the flap on the valve uncovers the vent, increasing vent flow. This means the patient is breathing out mainly against the atmospheric pressure as opposed to the treatment pressure. When the patient breathes in again the flow to the mask increases and the flap directs the flow from the CPAP device allowing treatment pressure on inhalation.

The problem with this kind of valve is that it creates a loud cyclic variation. The vent noise is loud on exhalation, when lots of air rushes through it, and quiet on inhalation. Additionally it only regulates the pressure, but does not relieve the pressure below the treatment pressure.

U.S. Pat. No. 6,080,461 discloses viscoelastic memory means and flow control valve used to produce a single-use, auto-destruct injection device. It is a memory flow control valve where the disk controls the flow by being forced opened and then reverting to its original solid shape due to its viscoelastic memory. The flow control valve of U.S. Pat. No. 6,080,461 has no applicability as a pressure relief valve in a PAP device.

There are no inexpensive alternatives to the currently available, expensive, high-level technology solutions for breathing comfort compliance. Cost is a major compliance issue for therapy. There are also no low-level technology breathing comfort devices currently available that are directed to improving compliance. Devising a low cost, low-level technology product would be beneficial for many patients.

SUMMARY OF THE INVENTION

A first aspect of the invention is to provide respiratory apparatus that is comfortable to breathe on. Another aspect of the invention is to provide a method and apparatus for supplying a smooth, comfortable pressure-time waveform of air through a respiratory cycle of a patient. Another aspect of the invention is to provide a mechanical valving arrangement that can be used to control the shape of the pressure-time waveform. Another aspect is to provide methods and apparatus adapted to control the rate of change of pressure with respect to time of a supply of air to a patient.

One aspect of the invention relates to a system for reducing exhalation pressure that may fit in an existing mask or airway path.

Another aspect of the invention relates to a system for reducing exhalation pressure that is compatible with a flow generator and humidifier system.

Still another aspect of the invention relates to a system and method for reducing exhalation pressure to produce an ideal pressure curve.

Yet another aspect of the invention relates to a system and method to deliver a treatment pressure on inspiration.

A still further aspect of the invention relates to a system and method for reducing exhalation pressure in a mask system that includes detecting a change from inspiration to exhalation, and triggering the reduction in exhalation pressure or detecting a change from exhalation to inspiration, and triggering a boost in inhalation pressure.

An even further aspect of the present invention relates to a mechanical, or electromechanical, self-contained system that systematically modifies the pressure waveform output at the mask for the purpose of improving comfort, specifically that it reduces the relative mask pressure during exhalation (or increases the relative mask pressure on inspiration) The system may be powered by batteries or AC power.

An even further aspect of the present invention relates to a mechanical, self-contained, powerless system that systematically modifies the pressure waveform output at the mask for the purpose of improving comfort, specifically that it reduces the relative mask pressure during exhalation (or increases the relative mask pressure on inspiration).

Yet another aspect of the invention relates a system and method to modify the CPAP waveform mechanically or electromechanically.

Another aspect of the invention is to systematically manipulate the pressure-flow waveform to improve comfort.

The systems and methods of the invention will benefit patients with SDB, including OSA, that are non-compliant to CPAP with normal lung function. The invention is suitable for home use. The invention may be used to encourage new CPAP users to start, and stay, on therapy.

One aspect of the present invention provides a mask system that reduces exhalation pressure without reliance on the flow generator. In one sample embodiment, the mask system detects the end of exhalation, and returns mask pressure to CPAP, without reliance on the flow generator. In another sample embodiment, the mask system comprises a mask incorporating valve functions. In yet another sample embodiment, the mask system comprises a normal mask, and a special valve arrangement that can be located on the mask or along the air pipe.

In a further sample embodiment, the mask system comprises user adjustable valve functions. In a still further sample embodiment, the mask system has reduced vent flow.

According to one sample embodiment of the invention, an apparatus for improving patient comfort during CPAP therapy comprises a venting arrangement configured to reduce expiratory pressure. In one embodiment, the venting arrangement comprises a normally closed demand valve that is openable responsive to patient inhalation. In one embodiment, the venting arrangement further comprises a normally closed pressure relief valve that is openable responsive to patient exhalation. In one embodiment, the venting arrangement further comprises an interlocking arrangement connecting the demand valve and the pressure relief valve such that only one of the demand valve and the pressure relief valve can be opened at one time.

A mask system for providing CPAP therapy to a patient, the mask system comprising a mask, a flow generator, a conduit connecting the mask to the flow generator, and a venting arrangement arranged to reduce expiratory pressure relative to the CPAP pressure. In one embodiment, the venting arrangement is mounted on the mask. In one embodiment, the venting arrangement is mounted in the conduit. In one embodiment, the venting arrangement comprises a normally closed demand valve that is openable responsive to patient inhalation. In one embodiment, the venting arrangement further comprises a normally closed pressure relief valve that is openable responsive to patient exhalation. In one embodiment, the normally closed pressure relief valve is mounted on the mask. In one embodiment, the venting arrangement further comprises an interlocking arrangement connecting the demand valve and the pressure relief valve such that only one of the demand valve and the pressure relief valve can be opened at one time.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIGS. 31 and 32 depict a valve according to still another sample embodiment of the invention;

DETAILED DESCRIPTION OF ILLUSTRATED EMBODIMENTS

Figure 1A:
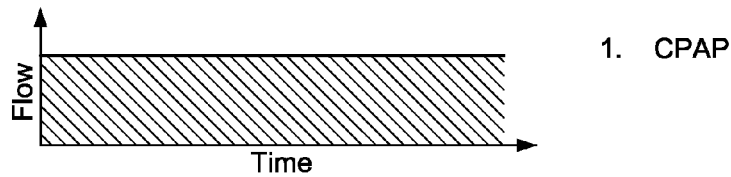
FIGS. 1A, 1B and 1C schematically illustrate basic differences in pressure change and flow with time for different types of PAP devices.
Figure 1B:
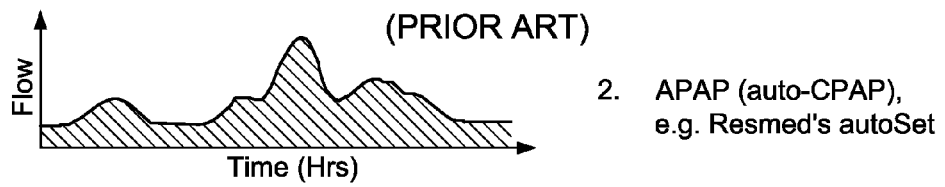
Figure 1C:
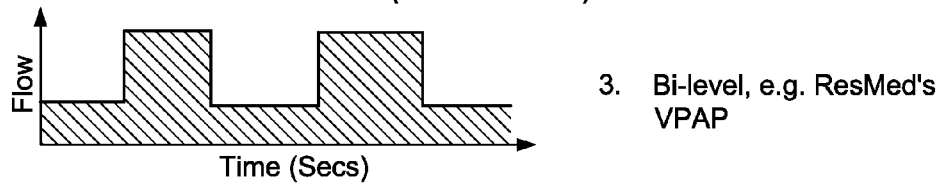
Figure 2:
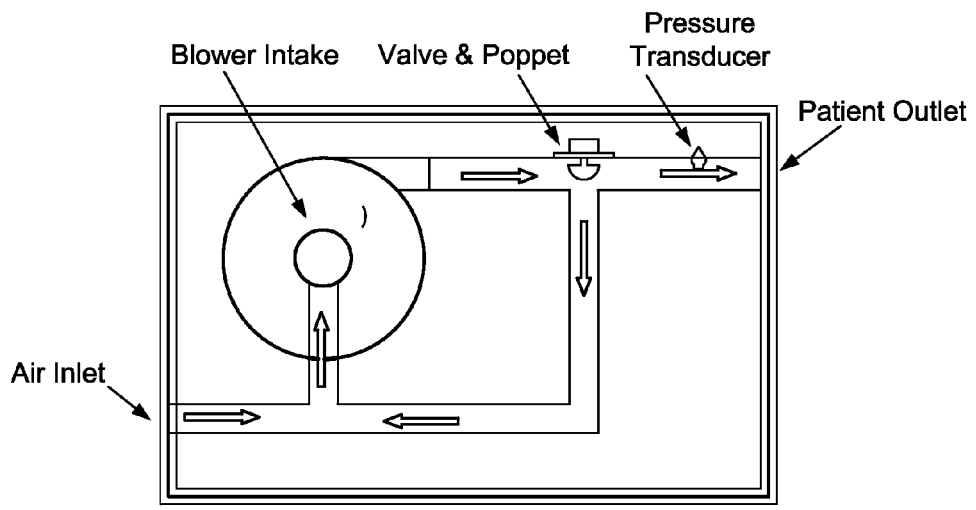
FIG. 2 depicts a known pressure swing reduction device.
Figure 3:
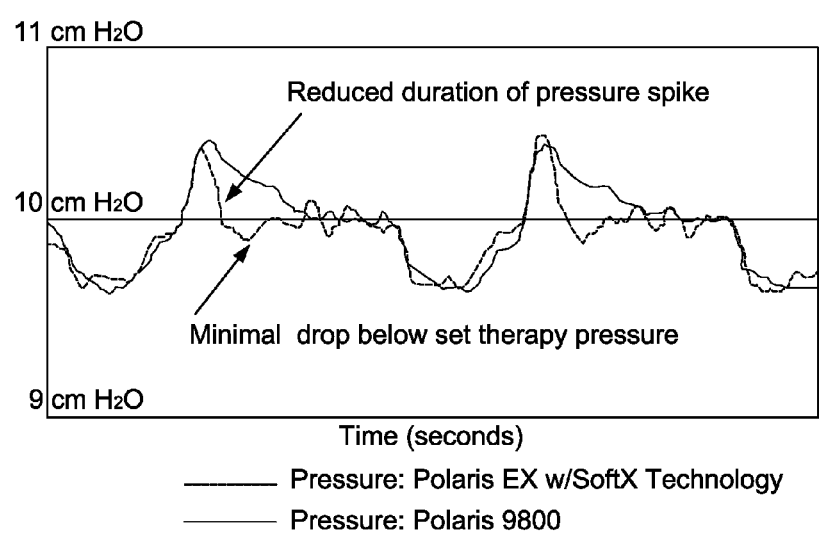
FIG. 3 depicts a pressure versus time relationship provided by the device of FIG. 2.
Figure 4:
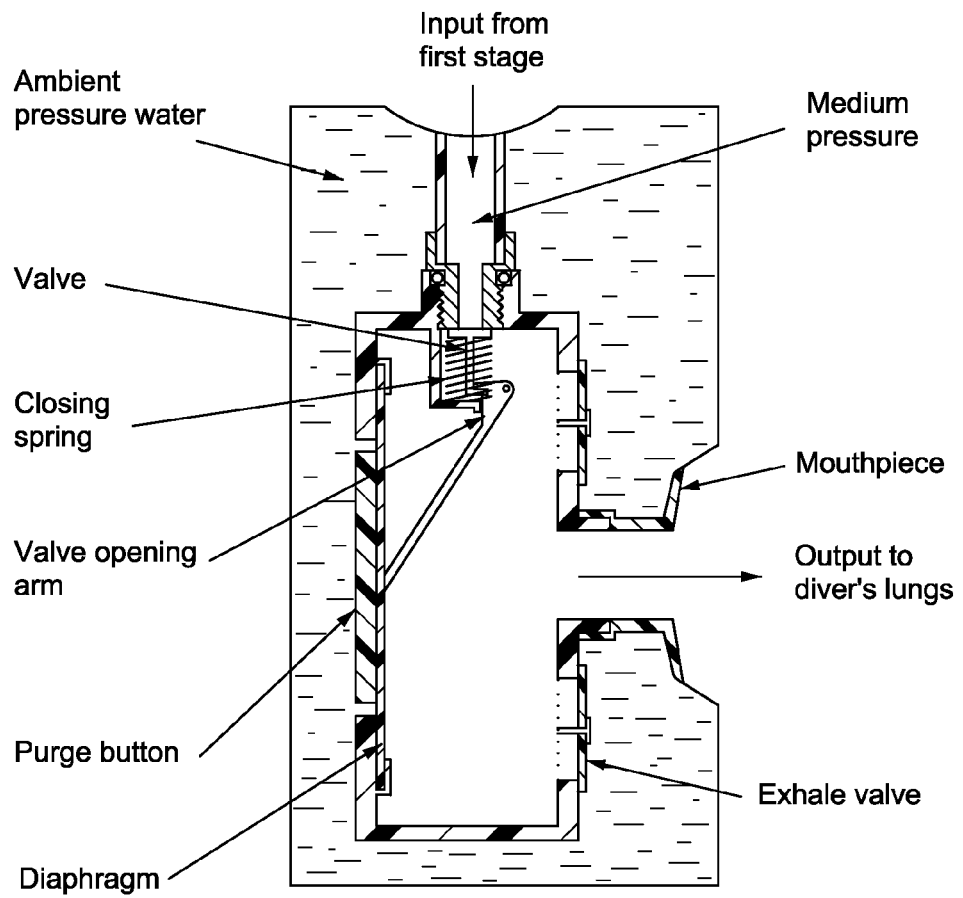
FIG. 4 depicts a known demand valve.
Figure 5:
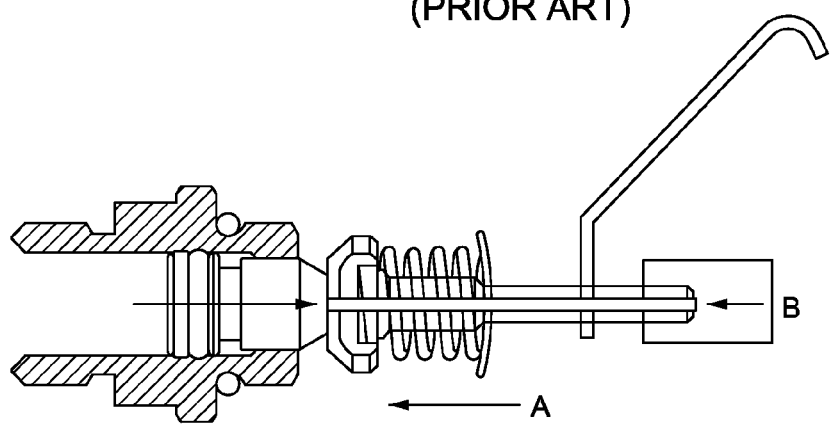
FIG. 5 depicts a known demand valve as provided to a scuba system.
Figure 6:
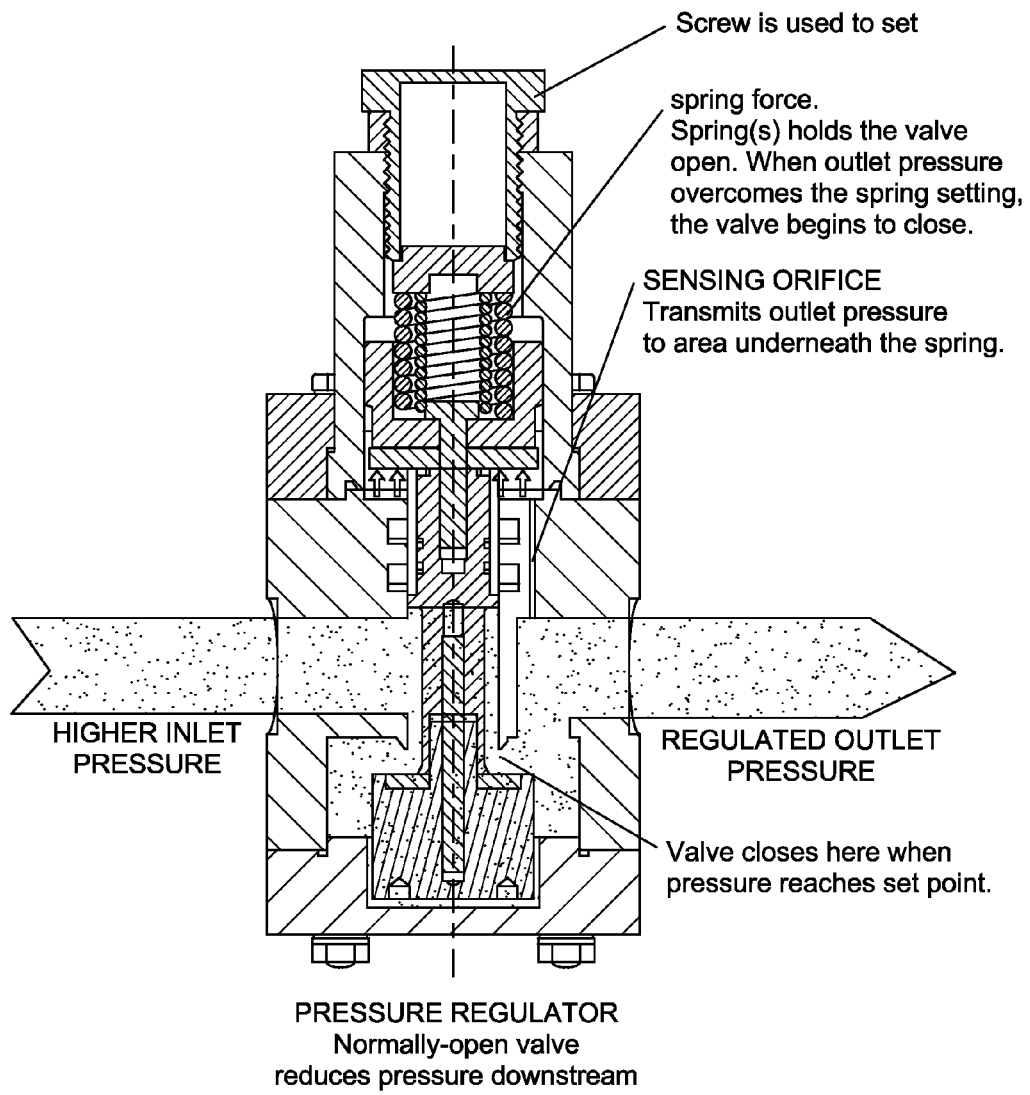
FIG. 6 depicts a known pressure regulation valve.
Figure 7:
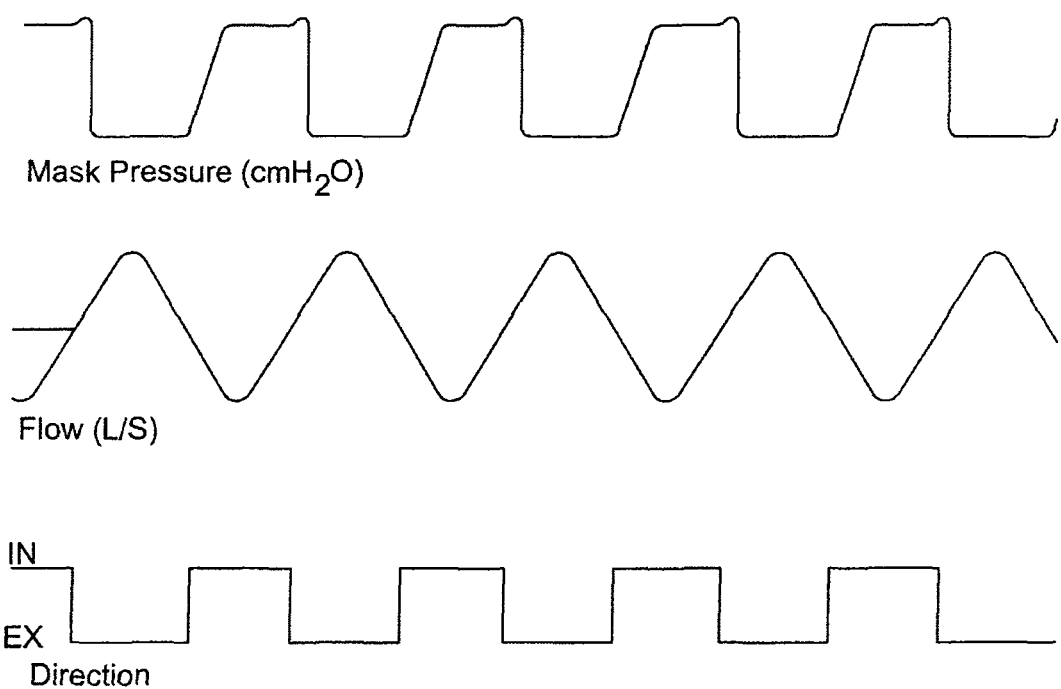
FIG. 7 depicts pressure, volume and flow curves associated with the mask of FIG. 50 according to sample embodiments of the invention.

The following description is provided in relation to several embodiments which may share common characteristics and features. It is to be understood that one or more features of any one embodiment may be combinable with one or more features of the other embodiments. In addition, any single feature or combination of features in any of the embodiments may constitute additional embodiments.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen. It is also acknowledged that the blowers described herein may be designed to pump fluids other than air.

Any type of relative pressure reduction during exhalation can improve patient comfort. The most effective pressure reduction is fast to reduce the pressure during the period of active exhalation, stays reduced during this period, and slowly returns to treatment pressure during the passive exhalation period.

Variable Venting

Generally speaking, the larger the vent holes, the easier it is to breathe out against the flow of pressurised breathable gas provided by the flow generator. Variable venting may include varying the vent area. As the patient breathes out, more holes are opened and the vent area gets larger and it is easier to breathe out.

Variable venting has many advantages. One advantage is that is simple to implement. Another advantage is that the valve may be either in the patient air path or in the mask, and the valve has a good reaction time and flushes out the $CO_2$.

Variable Venting—Seal Up Prongs On Exhalation

The patient breathes in through a first mask. When the patient breathes out, inlet prongs seal up and the patient breathes into a second mask which has a larger volume.

Variable Venting—Flexible Holes

Small holes, e.g. pin pricks, are formed in a thin, elastic membrane that forms a vent. As pressure increases during exhalation, the holes stretch open and permit the exhaled gases to be vented.

Variable Venting—Iris Vent

A vent may be formed as a circular vent-like iris. The vent constricts backflow during exhalation and at the same time opens to exhaust exhaled gases to the atmosphere.

Variable Venting—Staged Venting

A plurality of vents, for example three, may be provided in stages. Different pressures open different vents. The vents may be arranged so that the vents are opened by staged activation pressures.

Variable Venting—Leak

The mask may be configured to leak during application of a peak pressure. The mask lifts off face and leaks between the cushion and the frame. The mask may be provided with a piston and a slide valve to permit the leaking. The mask may also include an elastic headgear or gusset. Holes may be formed in the gusset, which may be formed of, for example, a foam ring around the mask to reduce noise. The gusset may be formed of a material that leaks more as the pressure increases.

Variable Volume

The volume in the mask may be changed during exhalation to reduce the pressure. As the volume of the mask is increased, the pressure is lowered which makes it easier to exhale against the flow of pressurized breathable gas provided by the flow generator.

Variable Volume—Sliding Piston

Figures 8, 9:
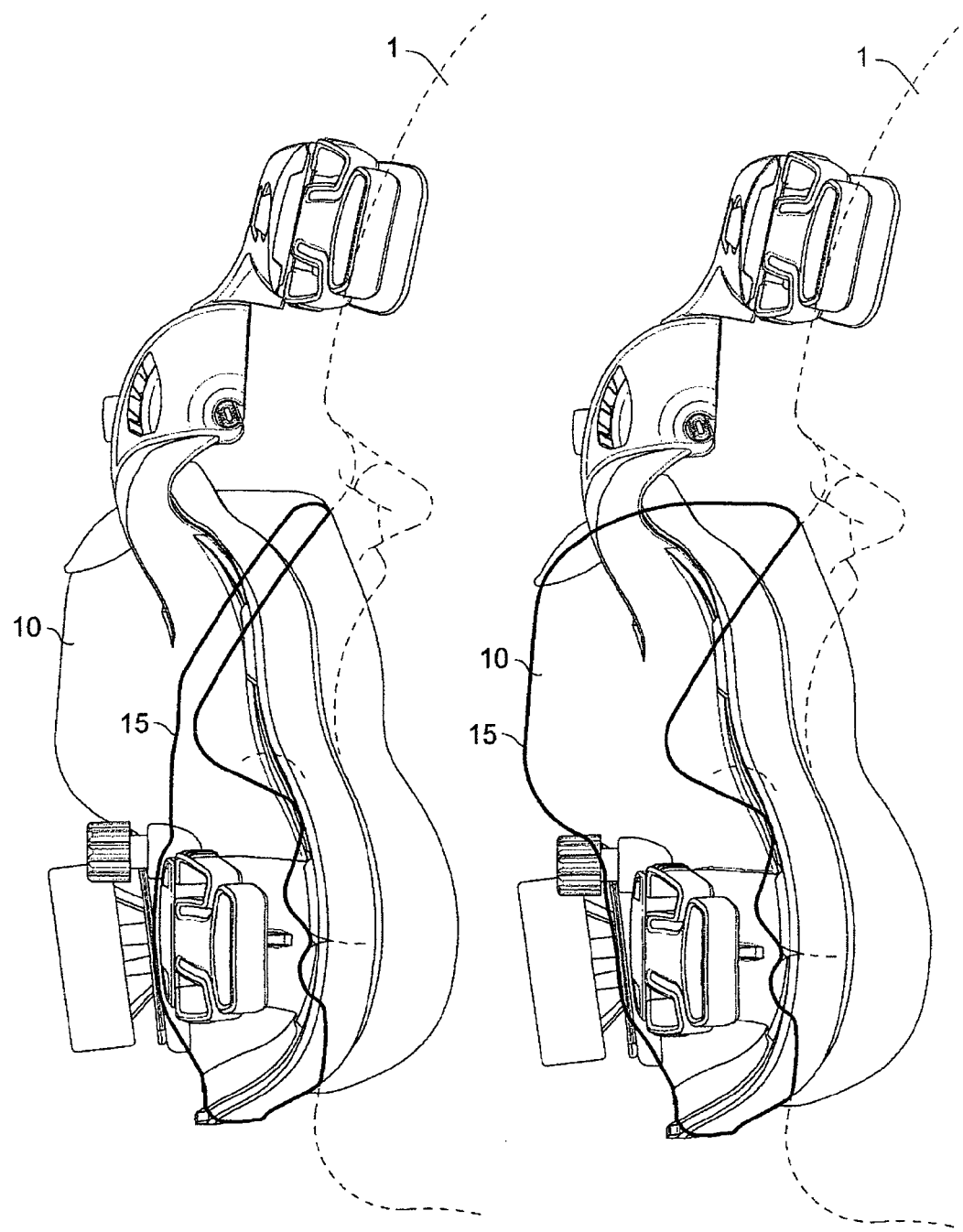
FIGS. 8 and 9 depict a mask according to a sample embodiment of the invention.

Referring to FIGS. 8 and 9, a mask 10 includes a piston, or diaphragm, 15 that slides and takes up volume in the mask 10 as the patient inhales and exhales. As shown in FIG. 8, as the patient 1 inhales, the piston 15 reduces the volume of the mask 10 to increase the pressure. As shown in FIG. 9, as the patient 1 exhales, the piston 15 increases the volume of the mask 10 to reduce the pressure and make it easier for the patient to exhale against the flow of pressurized breathable gas provided by the flow generator. The piston 15 may be triggered by, for example, heat or current. The piston may be formed of a material that becomes flexible at a predetermined temperature, or that flexes upon application of a predetermined current.

Flow Diversion

Figure 10:
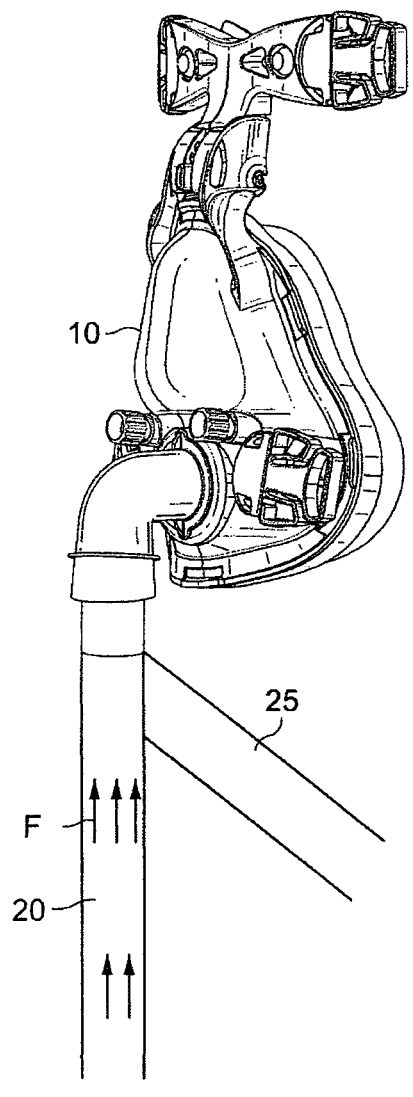
FIGS. 10 and 11 depict a mask according to a sample embodiment of the invention.
Figure 11:
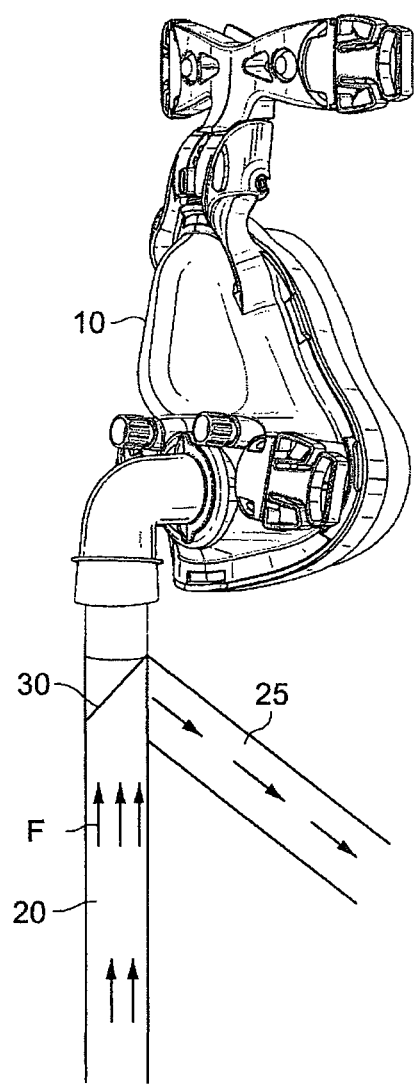

Referring to FIGS. 10 and 11, a first conduit 20 delivers a flow F of pressurized breathable gas from the flow generator to the mask 10. A second conduit 25 is provided for diverting flow from the mask 10. A flow diverter 30 is provided between the first and second conduits 20, 25 to direct the flow either to the mask 10 or to the second conduit 25. As shown in FIG. 10, during inhalation, the flow diverter 30 does not divert the flow of pressurized breathable gas from the mask 10 and the flow is delivered to the patient at the prescribed pressure. As shown in FIG. 11, during exhalation, the flow diverter 30 is moved to divert the flow of pressurized breathable gas into the second conduit 25 to reduce the pressure in the mask 10, making it easier for the patient to exhale.

The flow may be diverted from the flow generator to another system or outlet. It should also be appreciated that all, or some, of the flow may be diverted depending on the desired exhalation pressure. The flow diverter 30 may assume a variable position between the first and second conduits 20, 25 to vary the amount of flow that is diverted.

The flow diverter of FIGS. 10 and 11 is quiet and will not, for example, disturb the patient's sleep. As the flow is not vented directly to atmosphere, the pressure in the mask does not drop excessively. The flow diverter may also be used with a flap valve discussed in more detail below and may be incorporated with other exhalation pressure reduction devices and systems described herein.

Inlet Restriction

Figure 12:
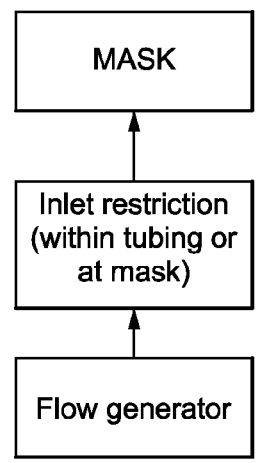
FIG. 12 depicts a process for reducing exhalation pressure in a mask according to the invention.

Referring to FIG. 12, the treatment pressure may only be delivered on inspiration or the expiration pressure reaching the patient may be restricted by a variable inlet restriction provided in either the conduit, or tubing, or the mask. The treatment pressures could be varied before they reach the patient. The EPR® algorithm on the ResMed CPAP device is based around this idea. One advantage of this sample embodiment is that it does not waste the pressure and air necessary for therapy by venting it to atmosphere, so it is comfortable and quiet.

Inlet Restriction—Testing

Various methods of restricting the inlet were tested. The results are shown in Table 1.

TABLE 1

| Aim (Question) | Method | Result |
| --- | --- | --- |
| 1. Would restriction of the tubes result in a pressure drop? | Attach flexible thin walled tubing into the circuit of a normal flow generator set up. Record pressure and flow rates. Squeeze the tubing and record the new pressure and flow rates. | Yes. The pressure drops with the restriction of tubing. Varying the area of the inlet varies the pressure in the mask as well as the flow that goes through the system. |

TABLE 1-continued

| Aim (Question) | Method | Result |
|---|---|---|
| 2. Does restricting the inlet cause the flow generator to act up? | See above - method in 1. | No. The flow generator does not try to compensate for the pressure drop when the inlet is restricted. |
| 3. What restriction is needed to drop the pressure? | In the modified flow generator circuit set up put a thick ring in the flexible tubing, thereby restricting flow to the internal diameter of the ring. Record the flow rates and pressure. | At no restriction, with a tube diameter of 17.42 mm, the pressure is 19.6 cm H2O and the flow is 54.2 L/min. With an area blocking the inlet to a diameter of 5.72 mm, the pressure is 14 cm H2O and the flow is 46 L/min. |

Vacuum Change

Reducing the pressure on exhalation may be done by any method that changes the resistance on expiration or compliance on inspiration, with the resultant effect of "power assisting" breathing. This would give a "boost" to inspiration and then back off the expiration pressure.

Figure 13:
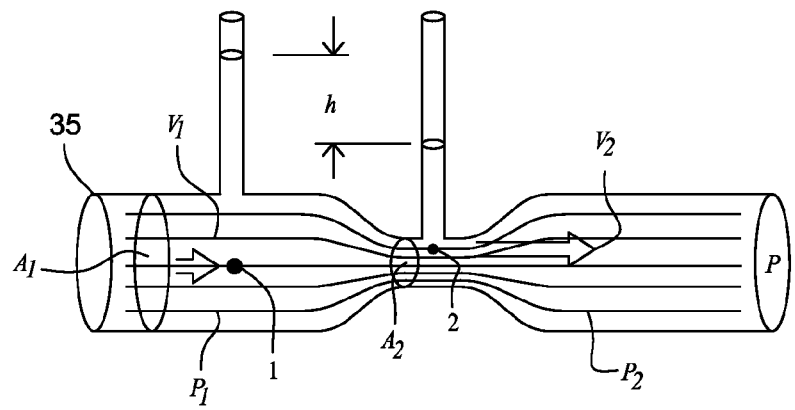
FIG. 13 depicts a relationship between flow and pressure in a venturi.

Referring to FIG. 13, a vacuum effect could be implemented using a similar concept as pool cleaners that utilise the venturi effect. This pressure differential could be used in the mask system. A venturi meter 35 is provided for the flow of pressurised breathable gas. The flow has a first pressure $P_1$ at a first point 1 that is higher than a second pressure $P_2$ at a second point 2 which is located at the throat of the venturi meter 35. The relationship of a first velocity $v_1$ of the flow to a second velocity $v_2$ of the flow is the same as the relationship between the first and second pressures $P_1$ and $P_2$. The pressure difference between the first and second points is determined by the height h of a column of liquid, for example water. A switch valve device could be used to switch from the high to lower pressure. Alternatively, the tube could be variably restricted, e.g. in a manner similarly to that discussed in relation to the inlet restriction.

Vacuum Mask

Using the Bernoulli effect, a venturi, as discussed above, may be used to suck air out of the mask during expiration. The valves discussed herein may act as a one-way valve or act to divert the flow to somewhere else. This would provide a simple, elegant solution. The use of a valve as a one-way valve or a diverter is also quiet, uses flow, not pressure, as a triggering mechanism, and may be set up to deliver puffs of air on inspiration and restrict flow to the mask during the expiration period. If the valve is set up to block the inlet rather than increase outlet venting, it would be more aesthetically pleasing in the tube and quieter.

Impedance Change

The reduction of the pressure during exhalation may also be done using impedance as the change mechanism. During inspiration, venting is inefficient. Therefore, there is less impedance through tube when breathing out, i.e. exhaling. Lower impedance may be obtained by different vent positions. For example, the vent may be placed right outside nostrils when breathing out. The vent may also be configured to change the direction of the air path. The air path has to have a change of direction for inspiration, and for expiration the air is straight out. Alternatively, a one way valve may be provided so that the air travels down the path when breathing in. As another example, "sails" may be provided to change with a change in the flow direction. The "sails" may deflect the air flow, or actuate a valve.

Balloon Valve

Figure 14:
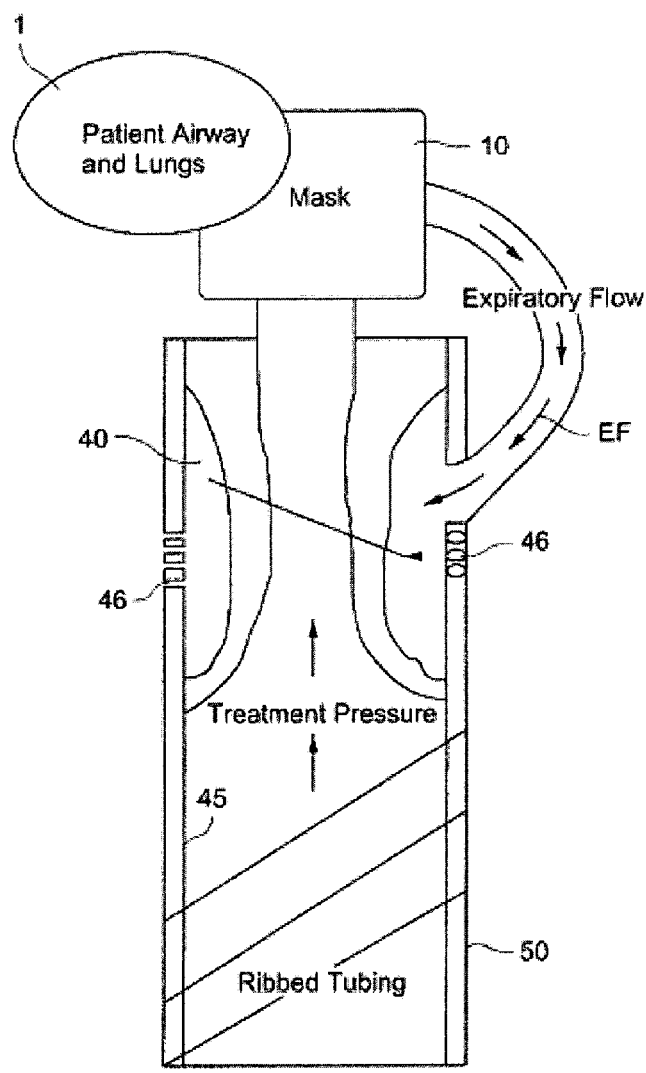
FIG. 14 depicts a balloon valve for restricting an inlet to a mask according to a sample embodiment of the invention.

This embodiment is based on the principle of inlet restriction discussed above. Referring to FIG. 14, during active expiration, expiratory flow EF is channelled into the air pocket balloons 40, which pushes on a thin, flexible tubing 45. This restricts the inlet air pressure. In the sides of the tubing 45, there are small leak holes 46 for the air to escape. The thin tubing is encased in stiff ribbed outer tubing 50.

Figures 15A, 15B, 15C:
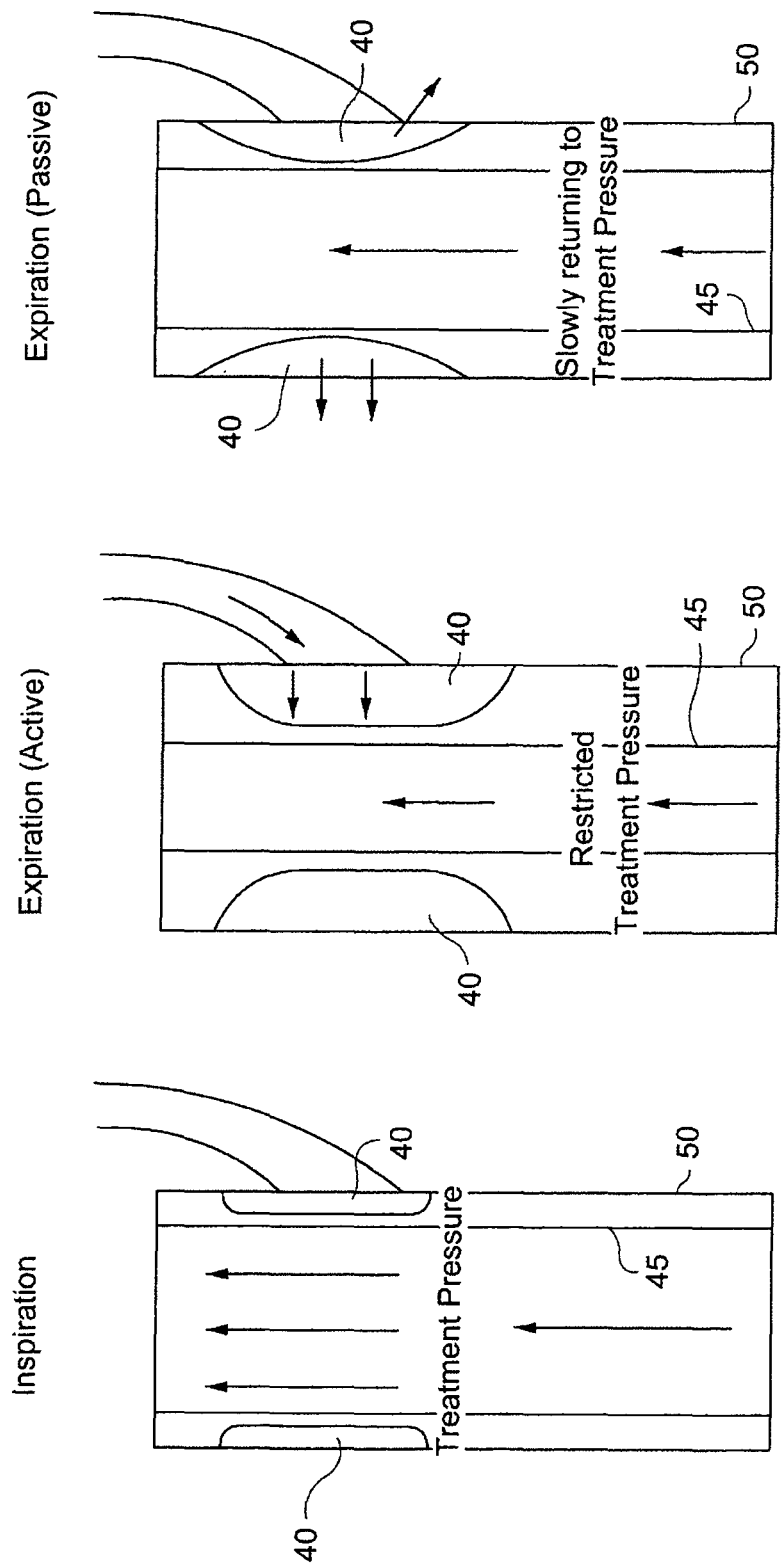
FIGS. 15a-15c depict the balloon valve in various stages of a patient's breath.

FIGS. 15a-15c depict the balloon valve in different phases of the breath cycle. During inspiration (FIG. 15a), the treatment pressure is delivered to the patient unrestricted. When the patient actively expires (FIG. 15b), the air fills the balloons 40, which restricts the treatment pressure. When the patient passively expires (FIG. 15c), the air in the balloons 40 slowly leaks out the small leak/vent holes, which slowly returns the treatment pressure to the patient.

The balloon valve shown in FIGS. 14-15c provides several advantages. It operates as a fail-safe because the leak always deflates the air pocket balloons if no air is blown into them, making pressure return to treatment pressure. The balloon valve is also quiet. There is no rush of expiratory flow, and the slow leak makes cyclic noise significantly reduced. The leak flow is multi-holed and diffuse, and therefore quiet. The air pocket balloons fill easily during active expiration, dropping treatment pressure quickly. During passive expiration, the slow leak means that treatment pressure is slowly restored. It is also possible to activate different numbers or sections of the air balloon pockets, e.g. by blocking or unblocking some, or all, of the leak holes 46. If an apnea occurs, there is no breathing so the air pocket balloons will empty and the treatment pressure will be restored.

The positioning concept of the balloon valve where the expiratory flow is diverted could potentially be used in other embodiments. The expiratory flow could be trapped to activate another valve, which produces a linear closing motion, for example.

Alternatively, valves that separated the different sections may create different pressures in different areas.

Dual Wall Tube

Figure 16:
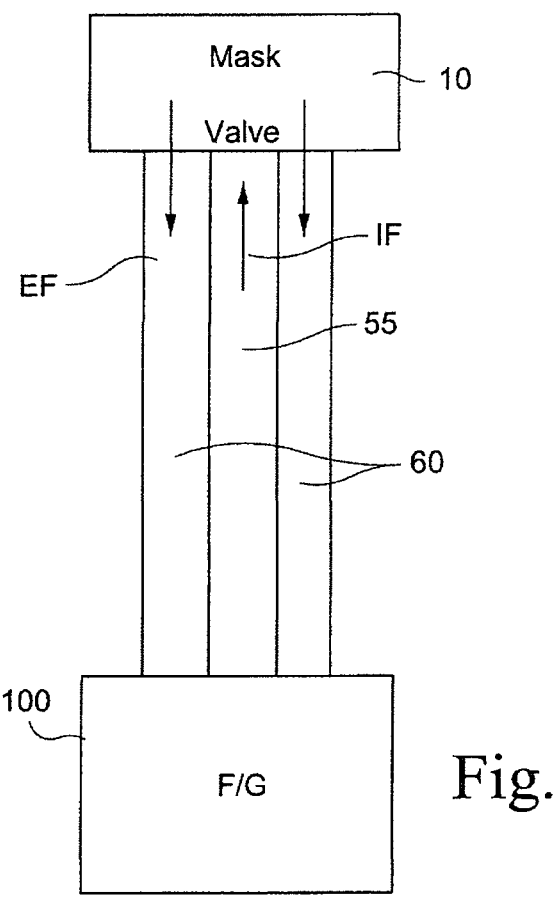
FIG. 16 depicts a flow diverter using a dual wall tube according to a sample embodiment of the invention.

Referring to FIG. 16, a dual wall tube uses the concept of flow diversion similar to the flow diversion discussed above with respect to FIGS. 10 and 11. The patient breathes in inspiratory flow IF, including the flow of pressurized breathable gas provided by the flow generator 100, through an inner tube 55. The person breathes out expiratory flow EF through the outer tube 60. The dual wall tube may also include a flow diverter to divert the expiratory flow down the tube. A ball valve blowing air inlet or an air stall down the pipe may be provided to reduce flow into mask.

The dual wall tube insulates the inner tube 55, providing warmer air, less rainout (where the humidity in the air condensates—rainout is usually caused by a temperature drop), and therefore higher humidity to the patient. The dual wall tube is also simple and easy as it is one part rather than having two tubes.

Propeller(s).

Backward Flow Propeller

A propeller may be provided to control the flow. One propeller is provided in the tube of the mask. On inspiration, the propeller would turn with the flow generator flow to deliver treatment pressure. On expiration, the expiratory flow down the tube would stall the propeller and the pressure in the mask would be reduced.

The backward flow propeller is simple and aesthetically pleasing. The backward flow impeller also prevents waste of humidified air. The backward flow propeller is also based on inlet restriction principles, which is the most viable parameter to manipulate for reduction of exhalation pressure.

Backward Flow Propeller—Variation

Instead of the propeller controlling the flow directly as discussed above, it could control a valve. The propeller would operate as discussed above, except that rather than reducing the pressure just on the reversal of spinning direction, the propeller would trigger another valve that would then reduce the pressure.

Misalignment Propellers

Figure 17:
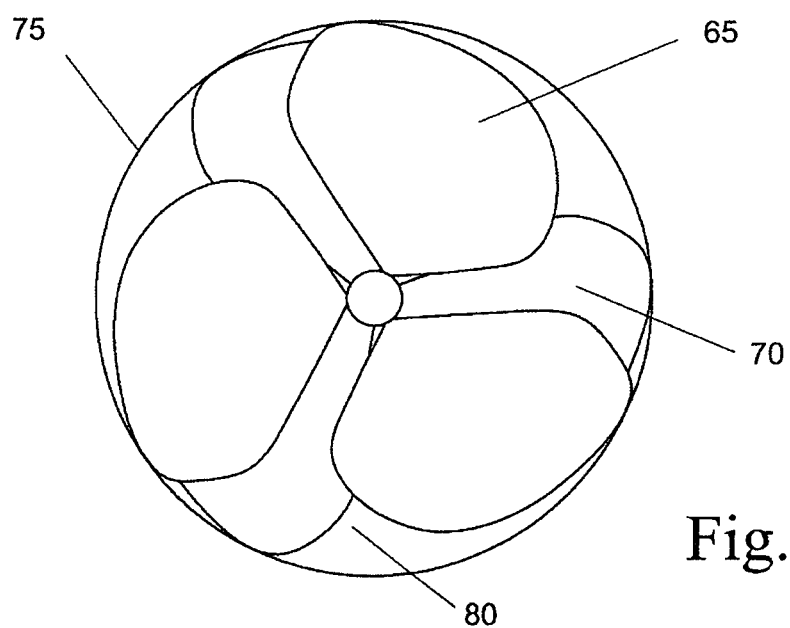
FIG. 17 depicts an arrangement for reducing the pressure in a patient interface during exhalation comprising two propellers.

Referring to FIG. 17, two propellers are provided in the tube 75 of the mask. As the patient breathes in, the propellers are aligned so the inlet is not blocked and the person receives treatment pressure. When the patient breathes out, the two propellers will misalign and the inlet will be blocked, reducing the pressure in the mask. Breathing in allows the two propellers to only spin one way, implemented by a ratchet or something similar that creates zero backlash.

The misalignment propellers are simple and aesthetically pleasing. They also prevent waste of humidified air. The misalignment propellers are also based on inlet restriction principles, which is the most viable parameter to manipulate to reduce exhalation pressure. The propellers are also easy to manufacture and safe, as they have no complex parts. A constant leak 80 provides an expiratory pressure.

Misalignment Propellers—Variations

Figure 18:
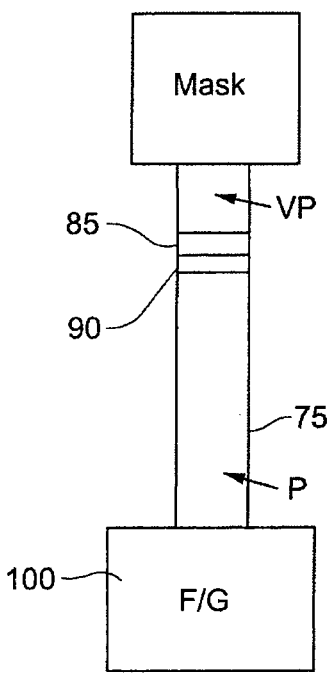
FIG. 18 depicts a variation of the arrangement of FIG. 16.

Referring to FIG. 18, instead of having two propellers, stationary tube block or propeller housing 90 and one rotating propeller 85 may be provided. Overall, the function would be similar to the two misalignment propellers, but have less complications and variables. There could also be multiple or variable pitch propellers, that fold up or change pitch, creating a streamlined effect of less resistance, on inspiration.

Volume Change Rotation Propeller

Figure 19:
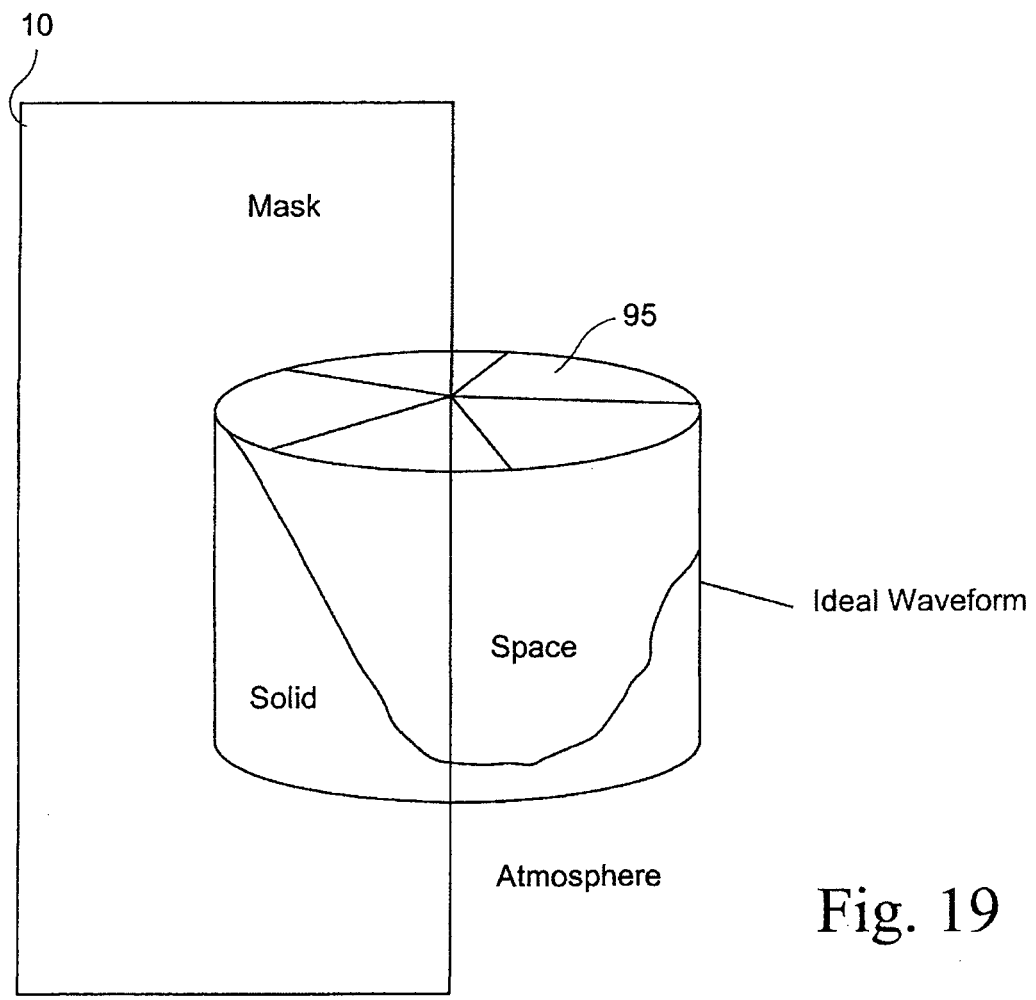
FIG. 19 depicts a vane-based venting arrangement in accordance with another embodiment of the invention.

Referring to FIG. 19, a propeller, or vane, 95 is hollow on the inside. The vane 95 rotates, 180° of it is solid, taking space when that half is on the inside of the mask 10. When the other side of the mask rotates the solid part is on the outside and the left over takes less space.

Electromechanical Hybrid Propeller

The propeller(s) of the embodiments discussed above may include a motor to brake or accelerate, acting like a power assist to breathing.

Viscoelastic Memory Valve

A viscoelastic material is a material that exhibits the characteristics of a viscous liquid and an elastomeric solid. Organo-silicone (e.g. SILLY PUTTY®), chewing gum and polyurethane memory foam are examples of these materials. Additionally, almost all polymers exhibit viscoelastic behaviour.

Viscoelastic material, i.e. memory foam, is sensitive to pressure and will change shape. There are also varying densities of memory foam. For example, memory foam may be obtained in 3, 4, 5.3, and 6 lb/ft$^3$. The foam may be used as a valve. As the pressure gets higher, the foam condenses, opening the valve at a rate varied with the pressure. This would allow the vent flow to be controlled by pressure in a rate proportional to patient breathing profile.

Memory foam provides an acceptable solution to reducing the pressure at the mask during exhalation, but presents some design considerations. For example, memory foam may give off a distinct chemical odour, which people may find unpleasant. The odor fades with airing, although some people may remain sensitive to it. Depending on the chemicals used and the overall density of the foam, memory foam can be firmer in cooler temperatures and softer in warmer environments. Higher density memory foam will react with body heat and allow it to mould itself to the shape of a warm body within a few minutes. This may not be ideal as the setting of the foam would be temperature sensitive and not work in different temperatures.

Figure 20:
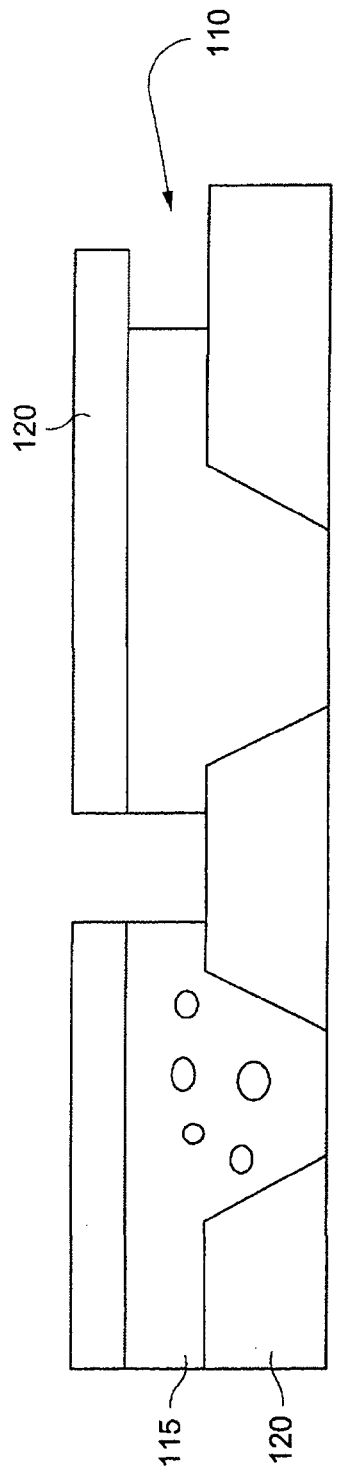
FIGS. 20 and 21 depict a valve according to a sample embodiment of the invention.
Figure 21:
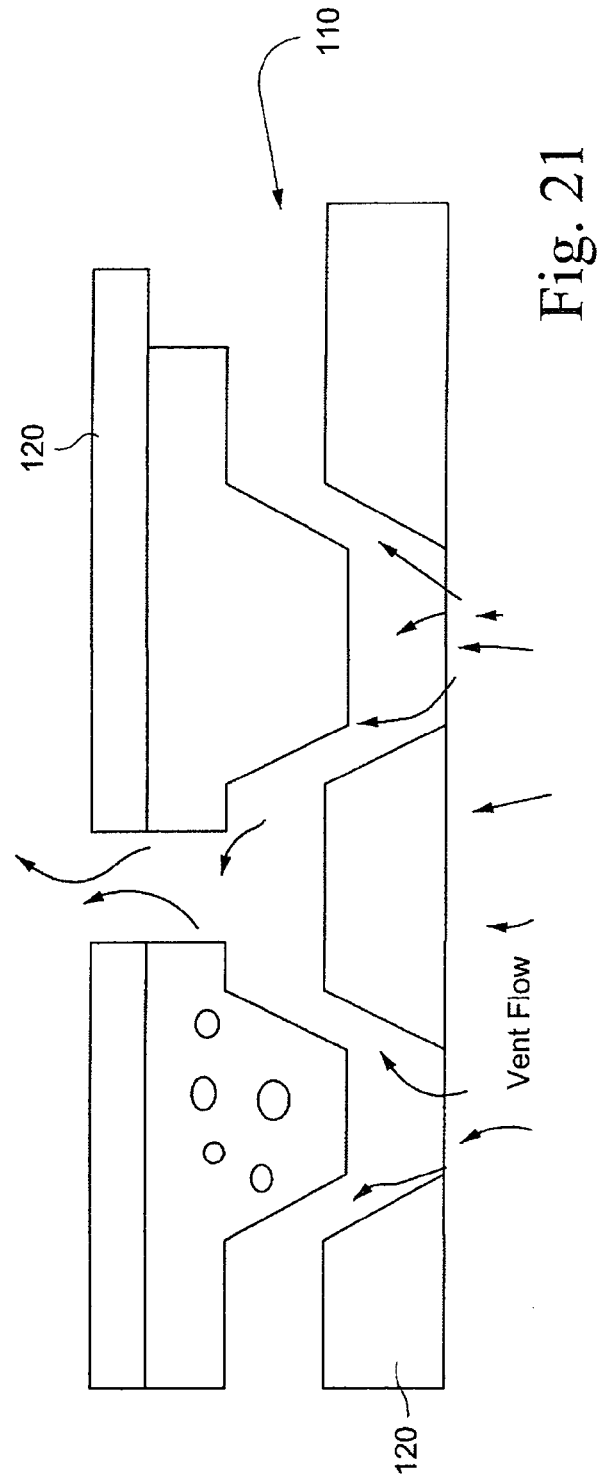

Referring to FIGS. 20 and 21, a vent 110 includes a body 120 and a memory foam 115. When the patient breathes in, the mask is at default, as shown in FIG. 20. The memory foam 100 is not compressed, and therefore takes up all of the vent space. When the patient breathes out, as shown in FIG. 21, the pressure in the mask will increase above treatment pressure. The memory foam will compress, taking less space and allowing flow out of the vents. The pressure would be reduced. As the memory foam slowly reverts back to its original shape, the flow is restricted and the pressure slowly comes back to treatment pressure. Alternatively, the pressure may be used to trigger a mechanism to compress the foam, and then mechanism is released and the foam is slowly allowed to recover.

The vent 110 may have a multi-hole design, making it a quieter and more flow would be diffusive. The vent 110 including the memory foam is quiet, as no clicking or engagement of valve elements is necessary. The memory foam also makes graded changes, and moves with the patient breathing profile. With time, the vent goes back to the default position of FIG. 20 as long as the pressure is not too great to keep it open. The vent is also inexpensive, simple, and easy to manufacture, install and use.

Metal Shape Memory Alloys

Metal alloys may also be used as memory materials. Nickel-titanium metal alloys, such as NITINOL®, are an example. Metal alloys are used in heart surgery to form stents. The molecular arrangement of these metals change with temperature. They can be heated and formed into one shape, then cooled to form a second shape. After that, a material like nitinol will "remember" the higher-temperature shape. When it is heated past its transition temperature it will change to the higher-temperature shape.

Electric current can be used instead of heat. In the mask, pressure fluctuations could connect and disconnect a circuit that contracts or expands venting, or the shape of the mask, by expanding or contracting the metal. This may be powered by a small battery in the mask, for example.

Another application of this metal shape memory alloy may be to line a very compliant and flexible membrane, made of silicon for example, with strips of the metal. This membrane would be in the inlet tube from the flow generator to the mask.

The use of memory shape metal alloys provides a simple solution to reducing pressure at the mask during exhalation. The design is minimal as the vent is entirely within the tube or mask. This makes it aesthetically pleasing and lightweight.

All that is required is a small battery source that could be within the mask, headgear or clips so it is disguised.

Rubber/Silicone Membrane

Figure 22:
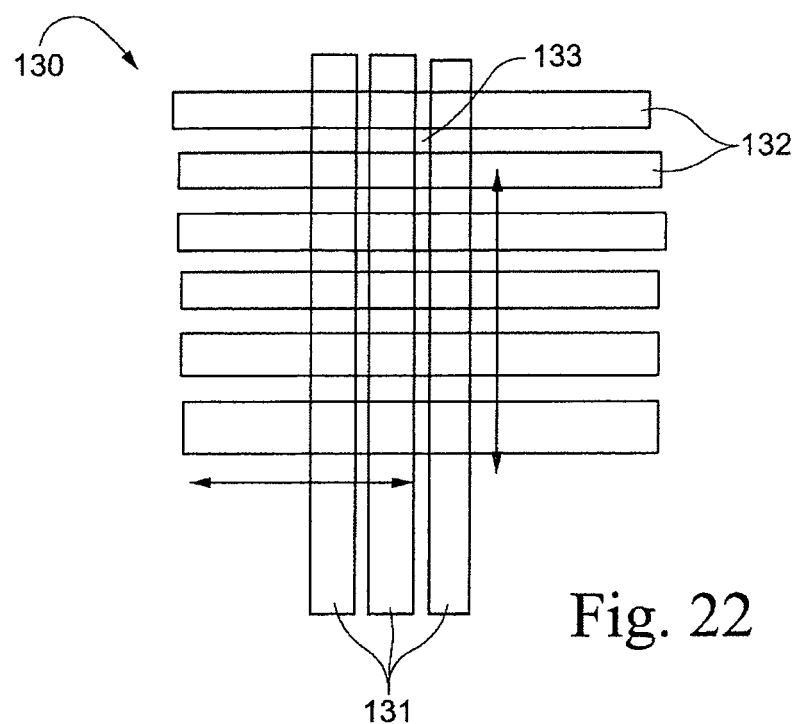
FIGS. 22-24 depict a venting arrangement according to another sample embodiment of the invention.
Figure 23:
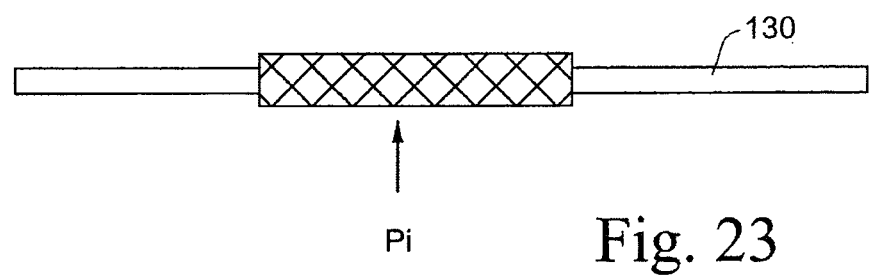
Figure 24:
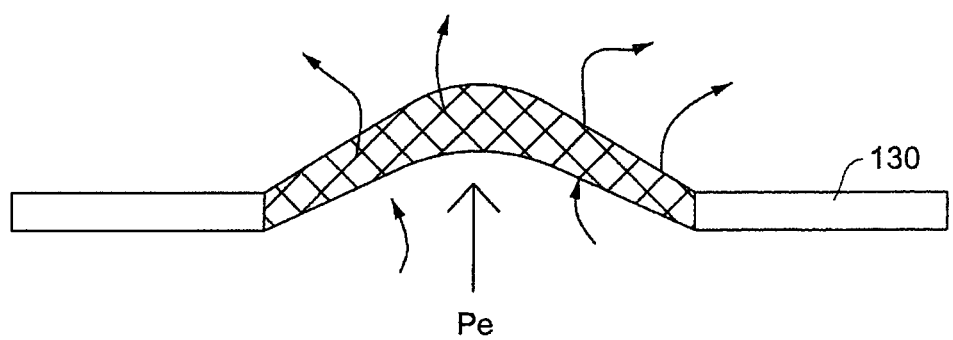

Referring to FIGS. 22-24, a rubber/silicone membrane 130 includes cross-hatched rubber/silicone fibers 131, 132. On inhalation the pressure Pi is low and the fibers are not stretched. Flow out of the vent(s) is limited, as shown in FIG. 23. On exhalation, the pressure Pe is higher and the fibres 131, 132 stretch and become thinner, making holes 133 (FIG. 22) where the flow out the vents increases, as shown in FIG. 24.

The membrane may be used with a variable mask volume, such as discussed above. The membrane and variable mask volume work in conjunction to lower the pressure.

The membrane vents and diffuses the exhalation flow and reduces the pressure at exhalation quietly. The membrane is inexpensive and simple to manufacture. The membrane may also be more reliable than memory foam.

Flap Valve

A flap valve may also be used to reduce the pressure during exhalation. The flap valve may be triggered by pressure and controlled by flow proportionally with the patient's breathing profile On inspiration, the flap is locked open, delivering treatment pressure to the patient. When the person breathes out, the pressure increases, unlocking the flap and moving it to the closed and locked position. When the pressure drops, the flap unlocks and opens.

The flap may be loosely locked, or clicked in, (e.g. held by a magnet) in the open position. When the mask pressure goes above the treatment pressure, i.e. when the patient begins to breathe out, the flap lock is moved, pushed open by a diaphragm divide, unlocking the flap.

As the patient breathes out, the flap moves to the closed position. As it opens to the full position, it clicks into the lock. This blocks the inlet and opens a vent to atmosphere, or to a second leaky chamber. When the pressure drops below a set minimum (e.g. set by a preloaded spring), the second lock is moved, unlocking the flap from the closed position.

The two possible uses of the flap valve are vented and non-vented. If the mask has a vent, then the flow to the patient is always net positive, or mostly net positive depending on the pressure level and the lung capacity of the patient. It takes a relatively low pressure or deep breath with a high tidal volume to get flow back down the tube. With a vented mask any flap would always remain open so the valve would only be closed if the flow generator turned off. The flap valve would thus operate similarly to an anti-asphyxiation (AAV) valve.

If the mask has no vent, when the patient reaches the end of the inspiration phase there is no flow. When the patient breathes out the flow is back down the tube. This change in direction of flow may be utilised by the flap valve.

The flap valve has several advantages. It is controlled by flow. It is fail safe with the flap open. The flap valve may also be used to control IPAP and EPAP settings The flap valve provides a combination of variable venting and restricting the inlet pressure.

Single Flexi-Valve

Figure 25:
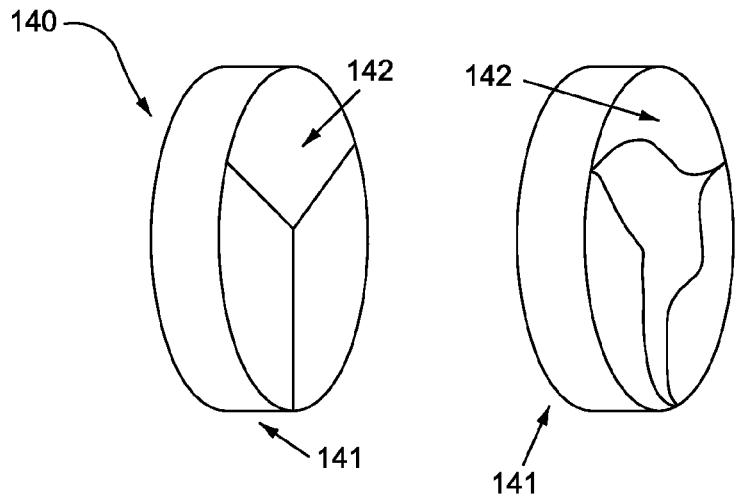
FIGS. 25a and 25b depict a venting arrangement according to still another sample embodiment of the invention, in the open and closed configurations respectively.

Referring to FIGS. 25a and 25b, a flexi-valve 140 works similar to a heart valve. The flexi-valve prevents backflow. When the patient breathes in, a flexible membrane 142 supported by a valve support 141 allows all the flow to go into the patient's lungs as shown in FIG. 25a. When the patient breathes out, the membrane 142 closes, as shown in FIG. 25b, and the flow is stopped from entering the mask and is breathed out the vents.

The flexi-valve is aesthetically pleasing, is inexpensive, easy to use and quiet.

Multi-Hole Flexi-Valve

A flexi-valve may include a multi-hole array. Thin membranes may cover the vent holes. Different pressures open different sized vents according to vent size and membrane thickness. The multi-hole flexi-valve may have flexibility through trigger pressures and combinations of holes used. For example, all the membranes may be configured to trigger (i.e. open) at high pressures, or some may be configured to trigger at lower pressures. The membranes may be in staged chambers to get a time delay or graded effect. The membranes may also be configured to open the valve to another volume. The holes would then shut and release the pressure to cycle through again.

The multi-hole flexi-valve has the same advantages as the flexi-valve.

Shock Absorber Valve

From the ideal pressure and flow curve, the pressure should be constant, release quickly and slowly recover. One-way damping may provide the ideal pressure and flow.

Referring to FIGS. 26-29, on expiration the shock absorber valve, or one-way damper, 150 works like a PEEP valve, quickly relieving the pressure. However, unlike a PEEP valve, the shock absorber valve 150 is very slow to restore the treatment pressure so it provides expiratory pressure relief. The thin, flexible plate 151 of the shock absorber valve 150 may be configured to control the flow to approximate the ideal pressure waveform.

Figure 26:
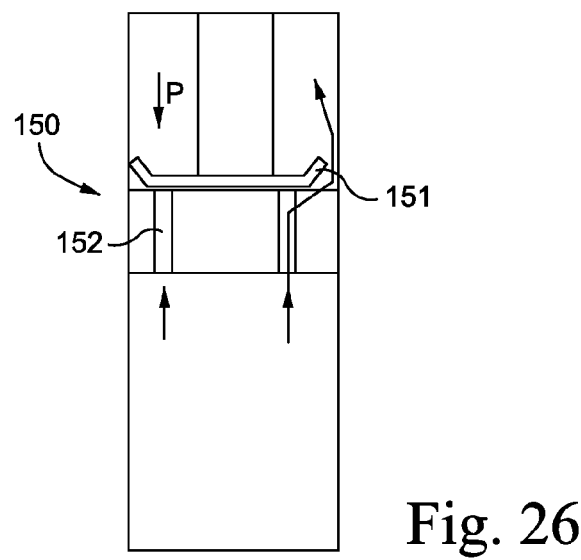
FIG. 26-29 depict a valve according to a sample embodiment of the invention.
Figure 27:
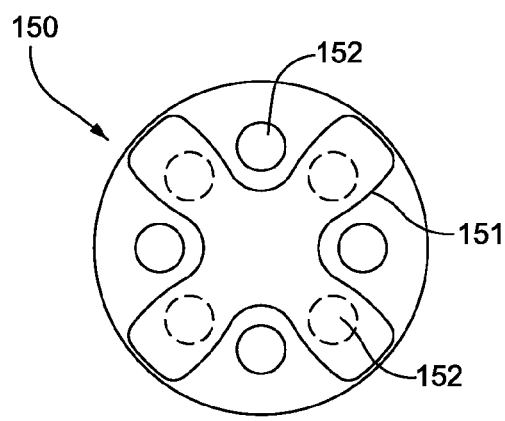
Figure 28:
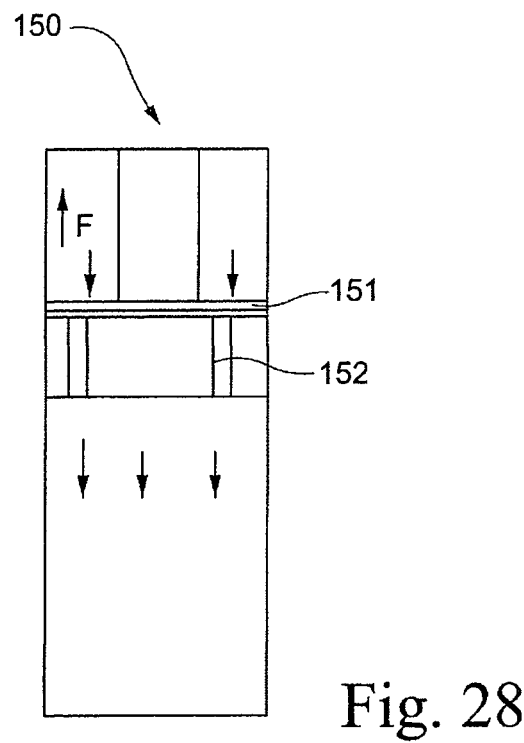
Figure 29:
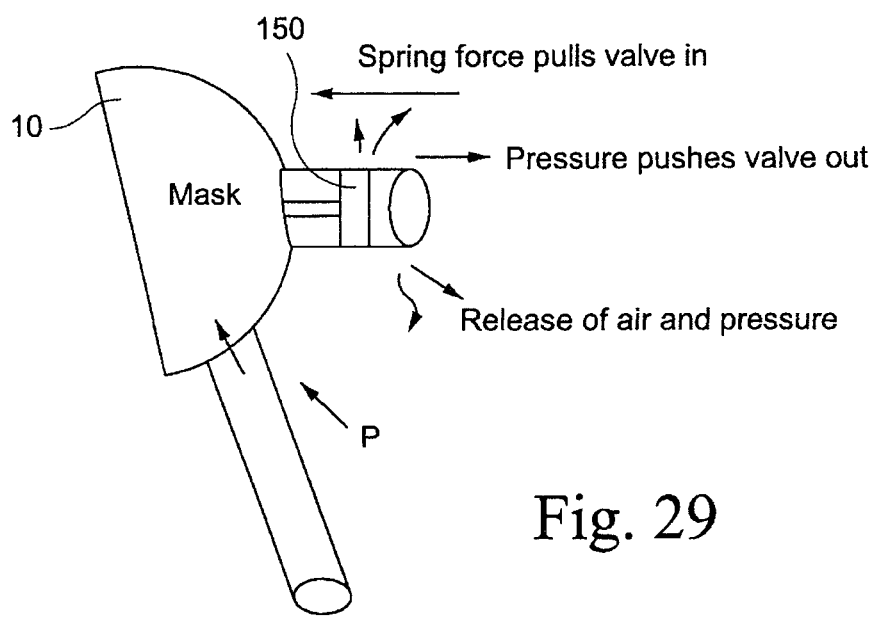

FIG. 26 shows the one-way damper on expiration. The pressure P acts to push the thin, flexible plate 151 down easily, relieving the pressure. The valve then slowly rises again. This may be aided by, for example, a spring system. The spring force preload may be adjusted for different pressures. The valve is slowed down as the thin, flexible plate 151 covers more holes 152 so there is more resistance to the valve returning to the default position (FIG. 28), which is a fail to safe position. This is shown in FIG. 27. There are holes that are covered by the thin plate only on inspiration, and some holes are open all of the time. The sizes and number of holes may be determined to operate in the desired way to produce the ideal pressure and flow curve.

Double Chamber

Figure 30:
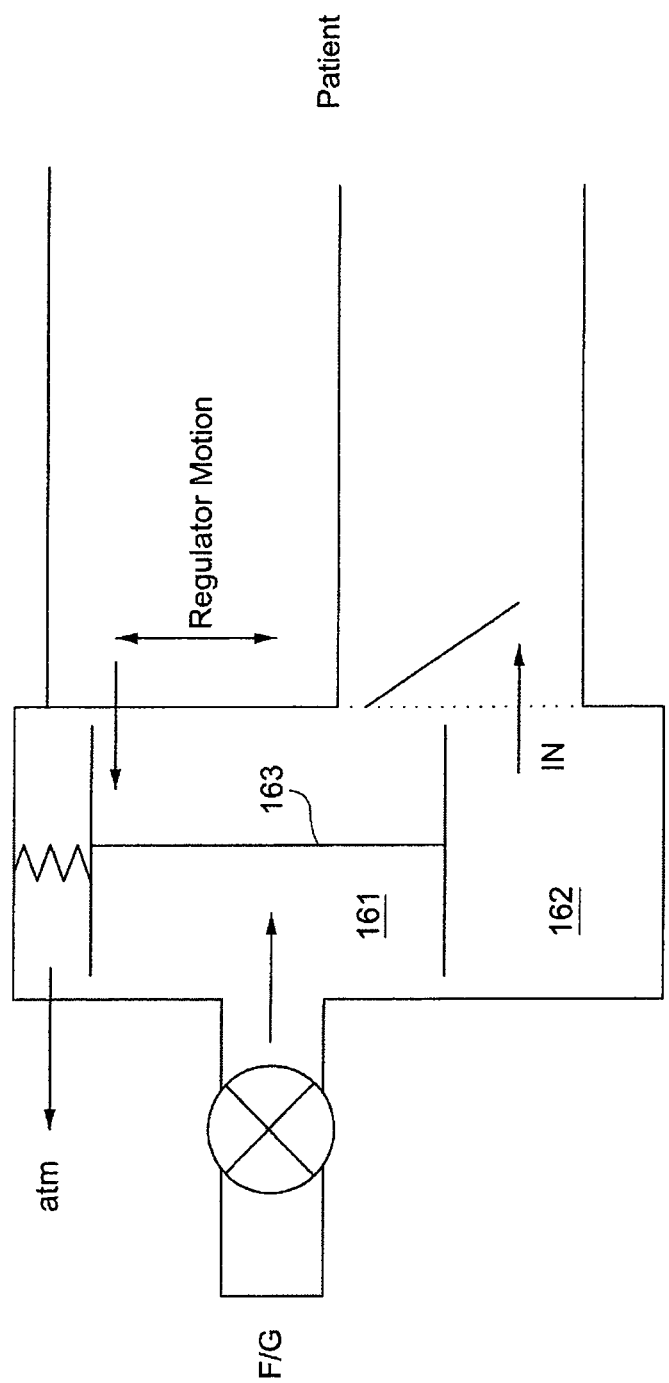
FIG. 30 depicts a venting arrangement according to another sample embodiment of the invention.

Referring to FIG. 30, two chambers 161, 162 drive each other to change the pressure in the mask. When the patient breathes out, the regulator 163 is turned off, blocking the flow from the flow generator. Then the valve is reset.

Modified Demand Valve

Referring to FIG. 31, as discussed above, the demand valve 155 has two components: the spring (or loading mechanism) 156, and the actuating element 157 which provides both sensing and control functions. The actuating element 157 is loaded by the spring 156 and senses the change in loading force from the environment.

The demand valve 155 of FIG. 31 has three separate components: the spring (or loading mechanism) 156, a sensing element 157 and a control element 158. The sensing element 157 loads the spring 156 which loads the control element 158 in turn.

The patient breathes in, which overcomes the spring force holding the valve shut. The treatment pressure is let in for the duration for the inspiratory phase of the breathing cycle. When the person stops breathing in, the spring force is no longer overcome so the valve shuts off the treatment pressure. The person exhales through one-way vents.

Referring to FIG. 32, the demand valve 155a may be modified so that there is a constant leak out of the demand valve 155 with fixed venting to balance the leak, and one way venting to balance the inhalation volume. The sensing element 158a is similar to the diaphragm in the scuba demand valve, and may be metal or plastic.

Figure 37:
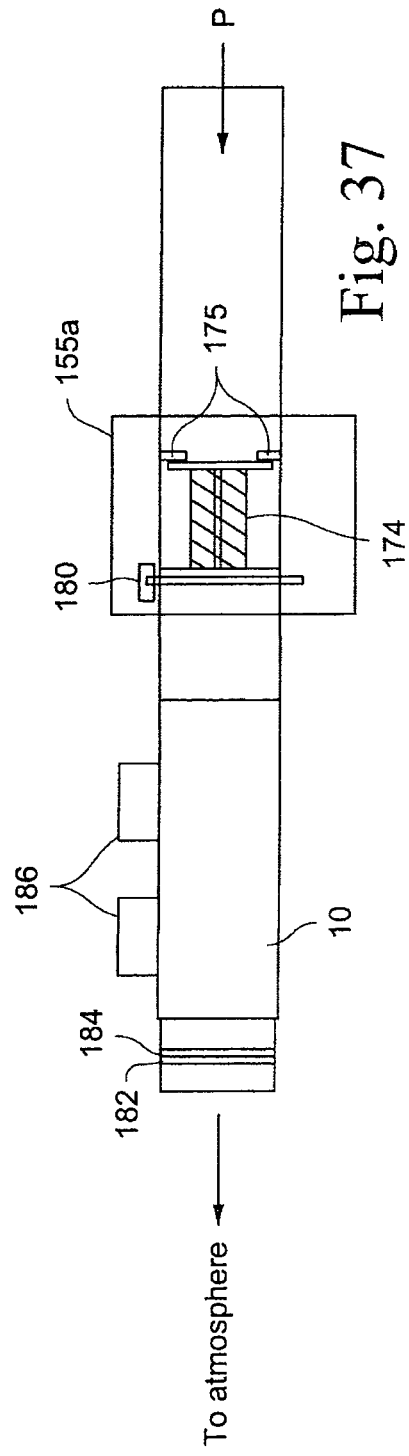
FIG. 37 depicts the demand valve according to FIGS. 34-36 in a mask system.

The modified demand valve of FIG. 32 is simple to produce, and may be fit into existing masks as in FIG. 37. The modified demand valve 155 also operates quietly as the exhaust is not excessive. The modified demand valve of FIG. 32 also separates inhalation and exhalation and follows a similar pattern to the ideal curve. The constant leak creates a minimum pressure so that there is always a residual pressure in the mask and provides a higher flush out rate of $CO_2$ One-Way Valve System Referring to FIG. 33, a one-way valve system includes first and second one-way valves 171, 172, respectively. The pressure A at the first one-way valve 171 is the flow generator treatment pressure. The pressure B between the first and second one-way valves is the pressure the patient would feel. Pressure C is the patient lung pressure, which will vary as the person breathes in and out. This is the triggering pressure that drives the valve function. The pressure D is constant, at atmospheric pressure.

Figure 33:
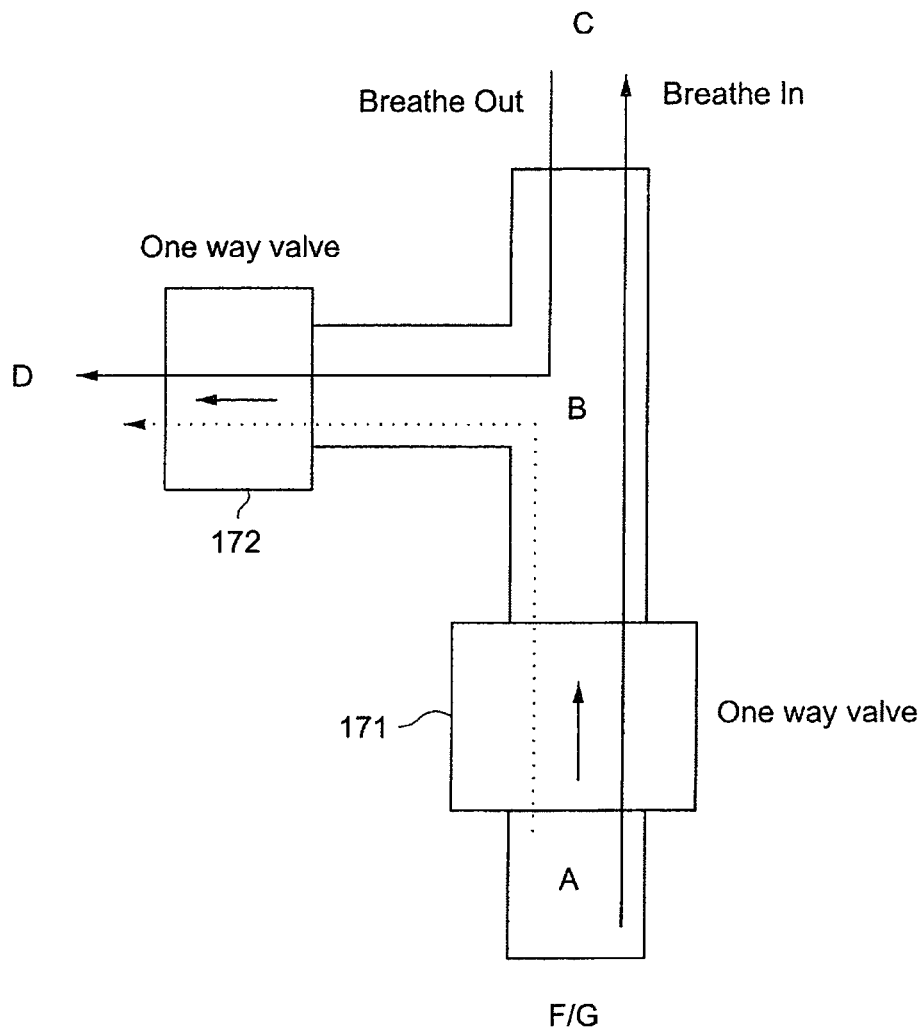
FIG. 33 depicts a one-way valve system according to a sample embodiment of the invention.

The dotted line represents the short circuit loop of a small leak that is desirable for $CO_2$ flushing and will still provide suitable therapy. The operation of the one-way valve system of FIG. 33 is described in Table 2.

Referring to FIG. 37, the demand valve 155a in the mask system works in conjunction with the one-way valve 182, 184 that allows the person to breathe out to atmosphere. The adjustment knob 180 changes the preload of the spring 174 by changing the default state length of the spring. As the knob 180 winds in, the spring 174 is pushed closer against the mechanical stops 175. The adjustment knob 180 allows the pressure to be changed to different treatment pressures.

As shown in FIG. 37, the mask 10 comprises nasal prongs 186. It should be appreciated, however, that any patient interface may be used.

The default state is when the closing spring is balanced against the force of the flow generator pressure. This closes off the pressure to the patient. As there is a small leak the pressure is not zero, but is significantly lower than the treatment pressure. From the default state, when the patient breathes in, the pressure differential between the flow generator pressure and the mask pressure will tip the balance of the closing spring. The spring will compress when the patient breathes in making a larger hole for air to flow, providing the patient with treatment pressure.

When the inspiratory effort tapers off, the balance between the closing spring and the flow generator pressure will be restored, closing off the pressure to the patient. The patient

TABLE 2

| State | Action | Result |
|---|---|---|
| Breathing in When the patient breathes in the pressure at C drops because of the larger volume of the chest cavity. Air from B rushes towards C. | Valve 172 closes due to the one way action of the valve; Valve 171 opens as the pressure at A is higher than B, and there is no mechanism to stop that action. | Patient receives pressure at A which is the desired result. A = B = C. |
| Breath hold (B = C) A is lower than B | Valve 171 will be closed; D is lower than B so flow will open to D; Valve 172 will open. | The valve 172 will open to atmosphere during breath hold, which would be good for comfort. |
| Breathing Out Pressure at C increases as the chest cavity volume decreases. | Pressure C is larger than B so air flows to B; Valve 171 closes as it is a one way valve; D is lower than B so Valve 172 is open. | Valve 171 will close, reducing the pressure during expiration. Valve 172 will open, allowing the person to breathe out to atmosphere. This is desirable. |

Demand Valve System

Figure 34:
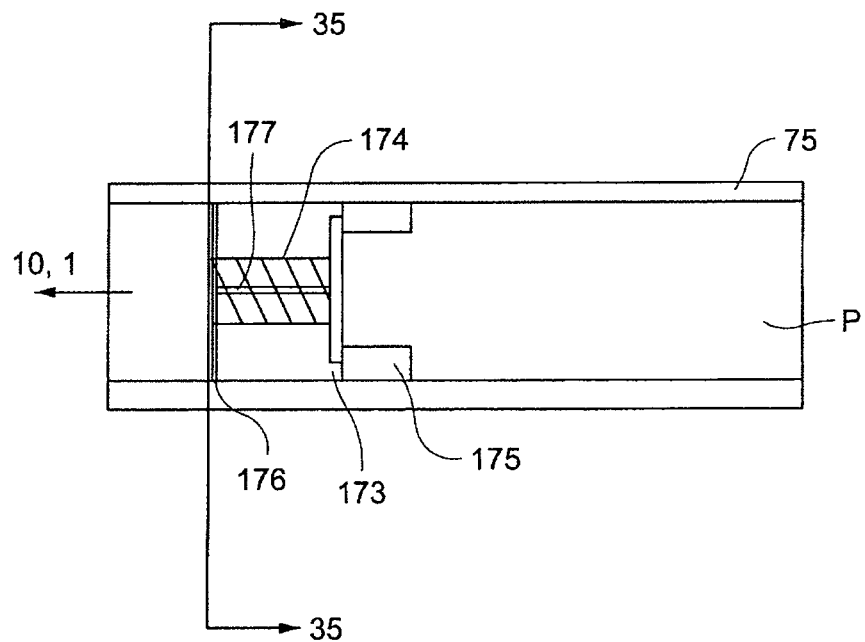
FIGS. 34-36 depict a demand valve according to a sample embodiment of the invention.
Figure 35:
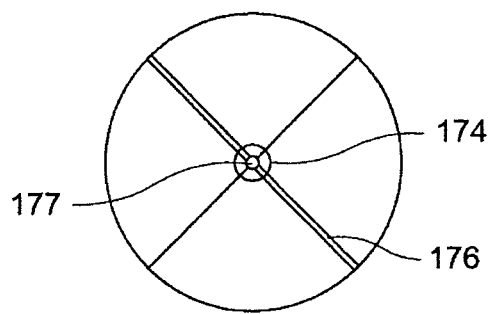
Figure 36:
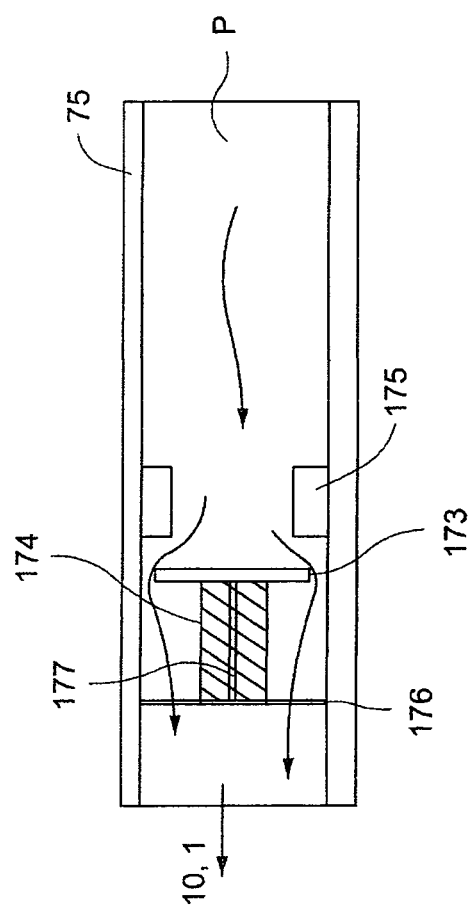

Referring to FIGS. 34-36, when the patient breathes in the sensing element 173, or diaphragm, of the valve is sucked in, opening the valve, which allows treatment pressure P to be delivered to the patient 1. When the patient exhales the diaphragm 173 of the valve blows out, which closes the valve against the stops 175. The flow is expired out a one-way valve. The force from the spring 174 opposes treatment pressure P to keep the valve 172 shut during expiration.

The sensing element 173 responds to the patient's breathing cycle. When the patient breathes in, the balance between the flow generator pressure P and the spring 174 is disrupted. The extra force applied to the diaphragm 173 overcomes the spring force, allowing the air path to open.

Referring to FIG. 35, the support struts 176 and support rod 177 are provided with as small a cross section as is possible so as not to increase resistance to the flow significantly, or interrupt the flow.

will then breathe out. As the patient breathes out, the pressure differential will activate the one-way valve and the patient will breathe out to atmosphere. The treatment pressure will only be restored when the patient initiates the breath. This way the effort required to trigger the device will never occur on expiration, only on inspiration when effort is naturally required.

Variations on the Demand Valve

A mechanism may be provided that locks one valve open and the other valve shut so that only one valve can be open at a time. A silicon flap or a spring loaded valve supported by a frame can be used instead of the lock.

The spring may be a plastic accordion-style spring. This has the advantages that it is plastic, so aesthetically better, and is safer and lighter. The spring constant is relatively low.

Just before the patient interface, after the demand valve components, e.g. the spring, there may be a safety mesh. This will catch any failed parts before the patient inhales them.

The adjustment knob may be encased, or locked down with a screw to prevent accidentally changing the treatment pressure.

Although the demand valve does not require a constant leak, the constant leak may be beneficial for the safety of the patient. The benefit of the leak is two fold. Firstly, it provides a constant washout of $CO_2$ and, secondly, it provides a baseline pressure for expiration. This makes sure that the pressure is recovered faster and minimises the chances of apneas occurring on expiration.

The constant leak also has a positive effect for humidity. As there is always some flow into the mask the moisture will not get trapped behind the block.

Figure 38:
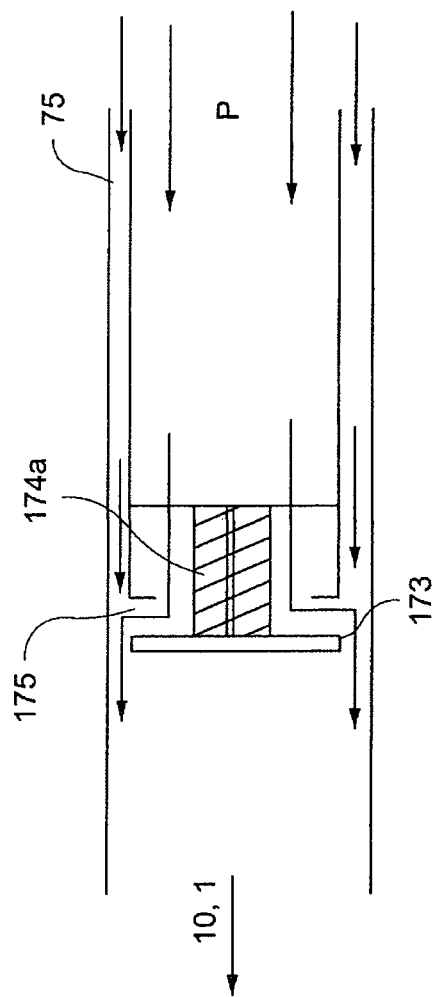
FIGS. 38 and 39 depicts a variation of the sample embodiment of FIGS. 34-36.
Figure 39:
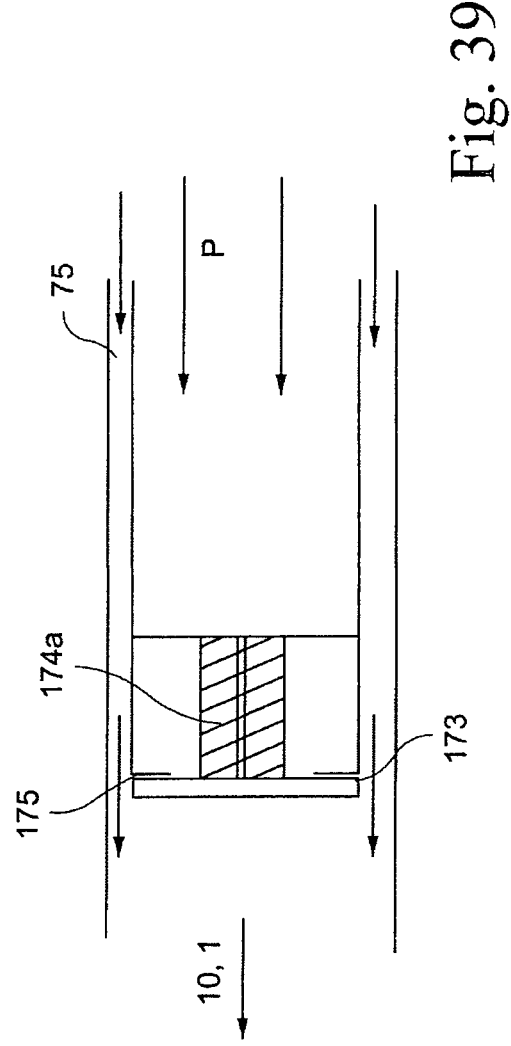
Figure 40:
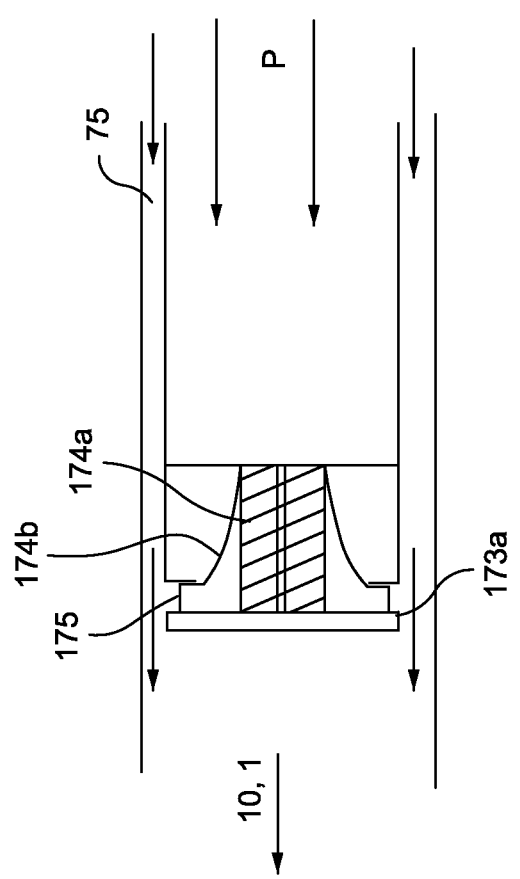
FIG. 40 depicts a variation of the sample embodiment of FIGS. 34-36 and 38-39.

An alternative to the demand valve including the compression spring is illustrated in FIGS. 38-40. As shown in FIGS. 38-40, the sensing element 173, or diaphragm, is biased into engagement with the stops 175 by a tension spring 174*a*. The alternative embodiments may also incorporate the dual wall embodiments discussed below and some include the taper idea, discussed in more detail below.

The dual wall tube of FIG. 16 may be incorporated into the demand valve system of FIG. 33 to introduce a constant leak through the system. Additionally, the dual walled tube helps with humidification, not only due to the leak, because it helps prevent rainout due to the insulating effect of the outer tube on the inner tube.

Referring to FIG. 40, the sensing element 173*a* may be provided with a taper 174*b* to improve comfort. The taper provides a more gradual difference in pressure, whereas no taper gives all or nothing approach to pressure difference. Although the tapered demand valve is shown in relation to FIG. 40, which includes a tension spring 174*a*, it should be appreciated that the taper may be provided to a demand valve system.

At least some of the sample embodiments discussed above are based on restricting inlet pressure and provide the following benefits. The sample embodiments allow flushing of $Co_2$. The sample embodiments also outlet flushed $CO_2$. The inlet may have a leak to help flush out the mask. The pressure is not dropped to zero, so treatment pressure is recovered faster. The valve(s) is not in a vulnerable position, so the patient cannot accidentally fit a finger in the mask and dislodge the valve. The valve also does not change the seal of the mask to the patient's face, or interfere with headgear. The valve(s) provides low exhalation noise and low motor noise as no air supplied by the flow generator is vented or wasted. The sample embodiments also do not waste humidity provided to the flow of pressurised breathable gas (e.g. air), and the gas is not too dry.

As the inlet is restricted, the sample embodiments are compatible with existing flow generators and may use flow generators with pressure sensors. In the sample embodiments, the position of the valve(s) means that the valve(s) is not vulnerable to covering. The valve(s) is also positioned not to be in the patient's eyes and obstruct the patient's vision.

The sample embodiments also allow flexibility in providing pressure to the mask. The sample embodiments are also insensitive to fluff, debris and humidity.

Constant Leak in Demand Valve System

Figure 41:
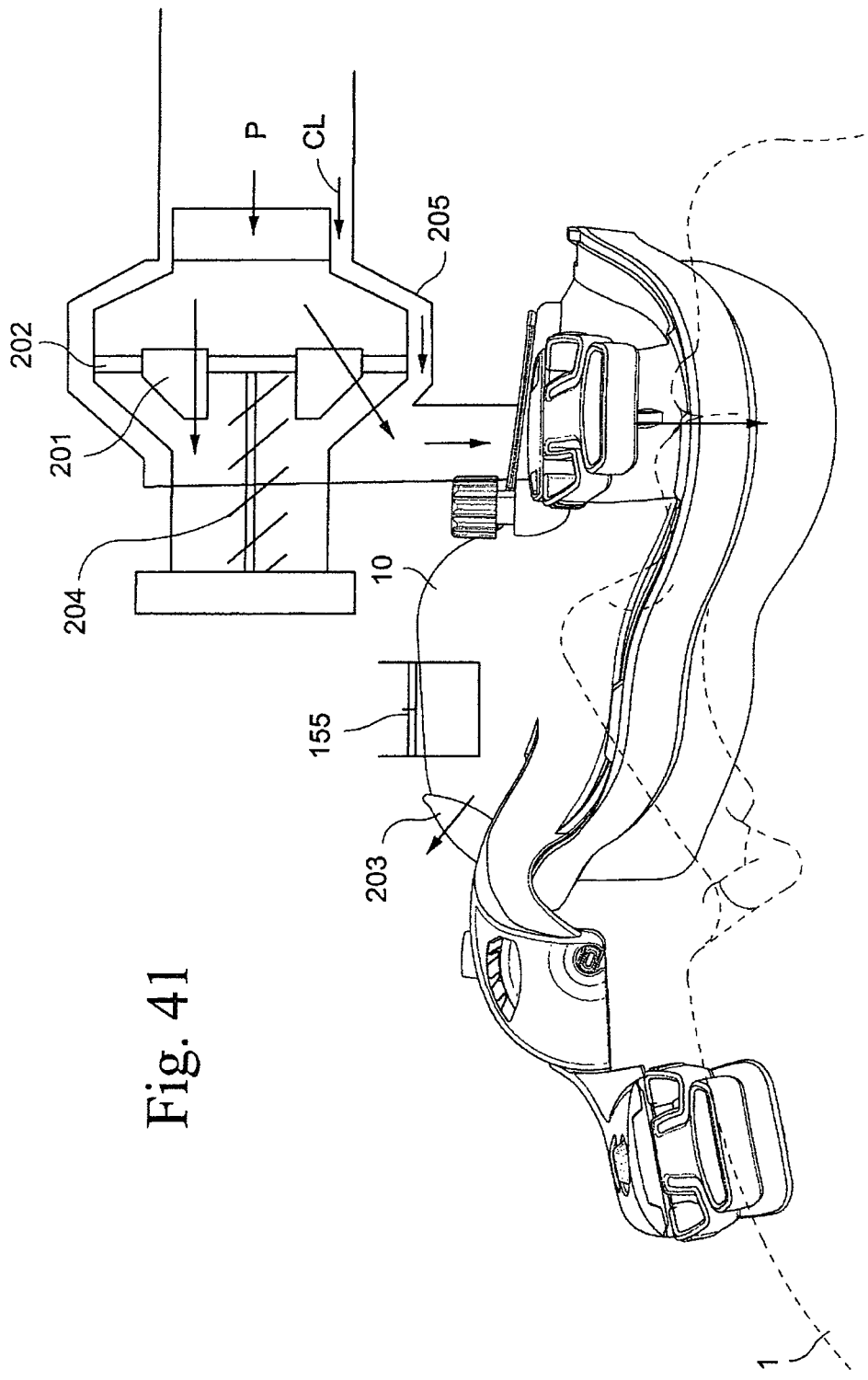
FIG. 41 depicts a demand valve system according to a sample embodiment of the invention during inspiration.
Figure 42:
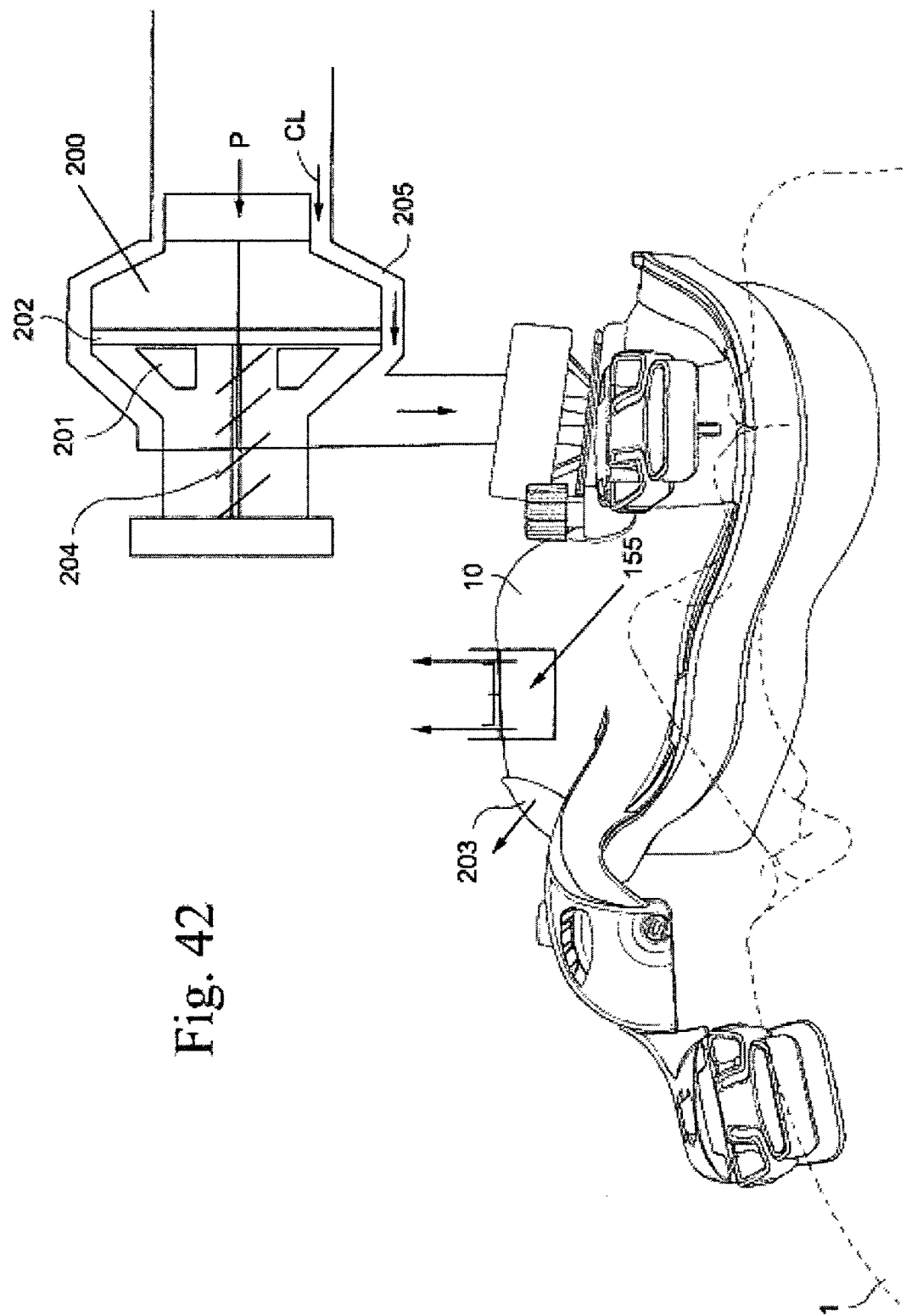
FIG. 42 depicts the demand valve system of FIG. 41 during expiration.
Figure 43:
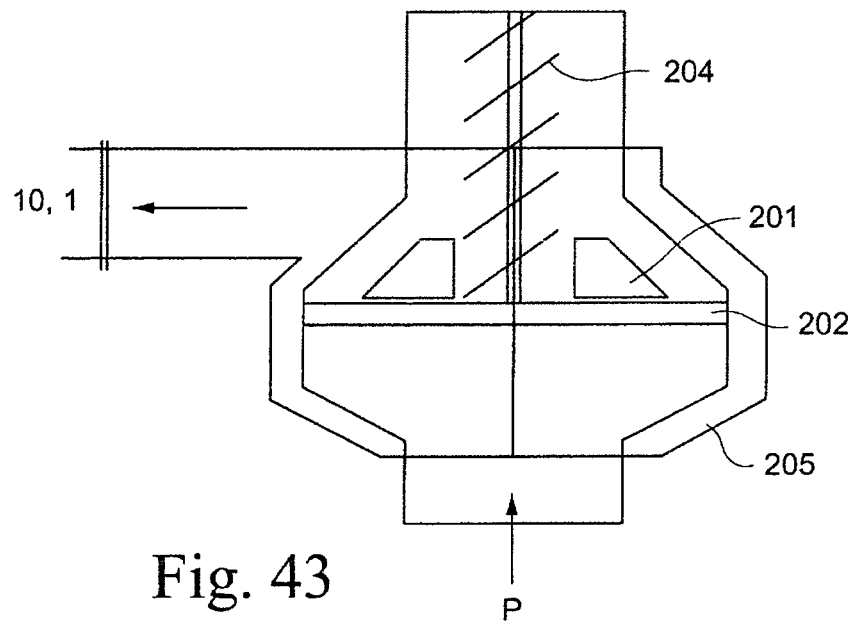
FIG. 43 depicts the demand valve of FIGS. 41 and 42.

Referring to FIGS. 41-48, a demand valve venting arrangement is shown. FIG. 41 depicts the mask 10 during inspiration and FIG. 42 depicts the mask 10 during expiration. A vent 201 shows the design for how the PEEP valve 200 is used in the demand valve concept. The air flows from the flow generator only when the valve 200 is activated by the patient inspiration effort. The diaphragm 202 lifts, allowing flow through the vents 201 and into the patient's airway. When the effort is no longer initiated, the flow from the flow generator is not delivered, and the patient breathes out through the one-way vent 203 to atmosphere. The adjustment spring 204 allows different treatment pressures to be used.

Figure 44:
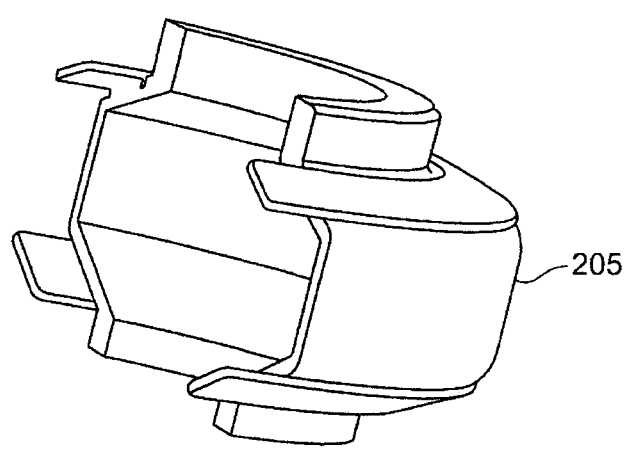
FIGS. 44 and 45 depict a cover for the demand valve of FIGS. 41-43.
Figure 45:
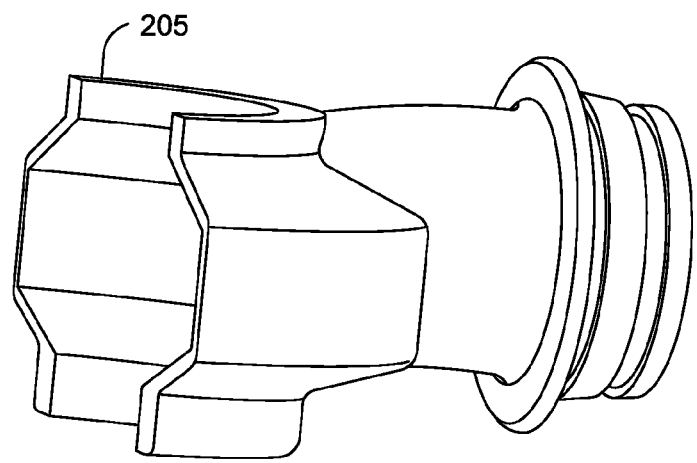

As shown in FIGS. 44 and 45, there is a parting line through the centre to allow the cover 205 to be placed over the PEEP valve 200.

Figure 48:
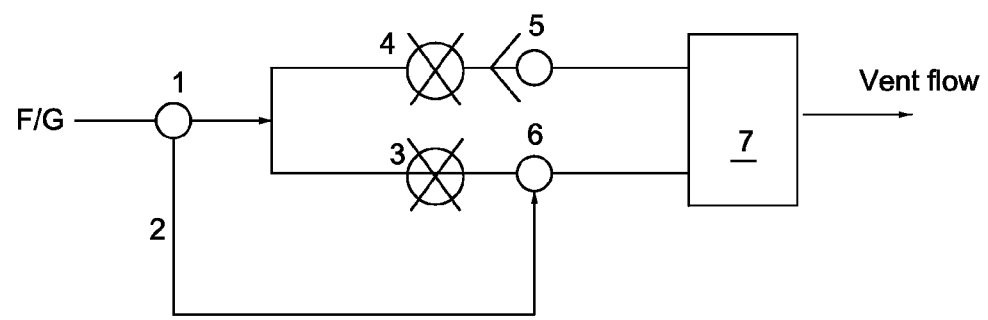
FIG. 48 depicts a demand valve system wherein the constant leak through the demand valve is modelled as a second flow source to the mask.
Figure 46:
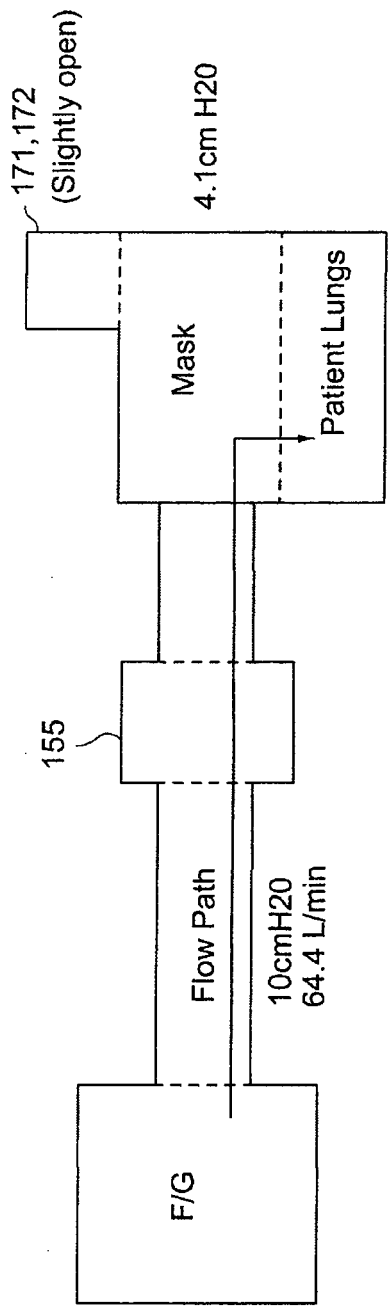
FIGS. 46 and 47 depict the flow path with example pressures in the demand valve system of FIGS. 41 and 42 during inspiration and expiration, respectively.
Figure 47:
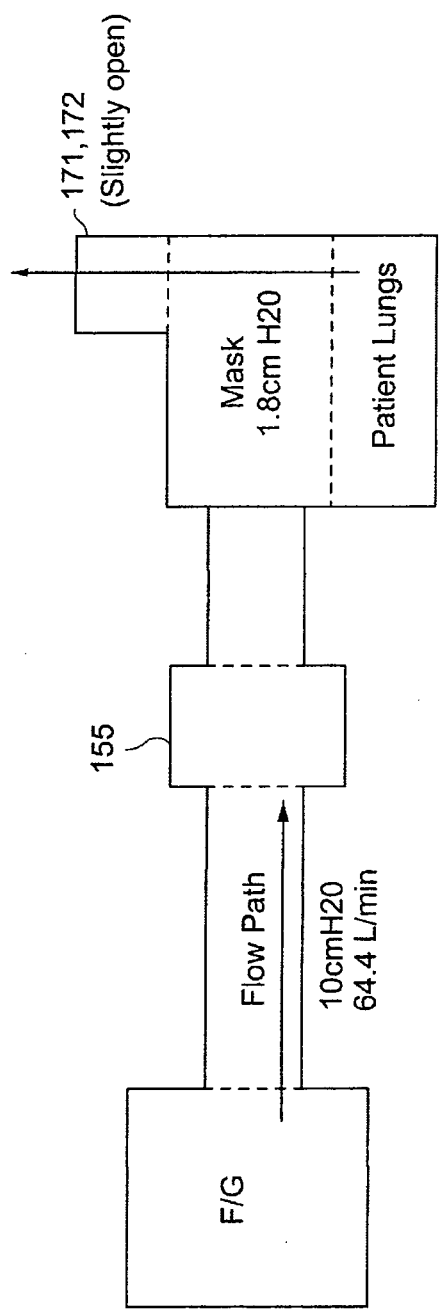

A model of toggle pressure is provided in FIG. 48. The flow generator supplies the pressure at the treatment pressure, for example 10 cm $H_2O$. The flow is split down the two paths to valves 3 and 4. Then there is a basic toggle between the expiratory pressure and the inspiratory pressure. The flow regulating valve 4 regulates the flow so that the pressure in the mask 7 is always a lower pressure; for example 4 cm $H_2O$. It has a one-way valve 5 down the line so that when the mask pressure is higher than 4 cm $H_2O$, the air does not go back down that line. This provides a constant, minimum expiratory pressure. FIG. 30 is an embodiment of this concept.

The flow regulating valve 3 is sensitive to the breathing cycle and provides the inspiratory pressure, for example; 10 cm $H_2O$. The flow differentials that are caused by the person breathing in and out are detected by the flow feedback valve 1. The pressure differential travels down the flow feedback line 2 and activates a flow switch 6. The flow switch 6 allows extra flow from the flow generator to pass through flow regulating valve 3. The flow regulator valve 3 regulates the flow to be the inspiratory treatment pressure, for example 10 cm $H_2O$.

Vent flow would have to be manipulated so that the mark pressure is sustainable while allowing adequate flush out of $CO_2$.

The system may be based on a series of diaphragms and spring valves. The flow feedback line 2 may create a vacuum in the line when the flow is low to pull open the regulating valve 3.

Figure 49:
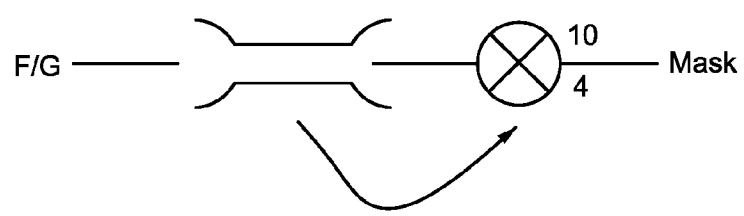
FIG. 49 depicts a variation of the demand valve system of FIG. 48.

The system could be simplified to have one line, and then toggle between two pressures, in this case 10 cm $H_2O$. This is depicted in FIG. 49. The high flow switch simplifies the two-source flow model of FIG. 48. The model could be simplified in other ways.

Interconnected Inlet and Exhaust Valves

Figure 50:
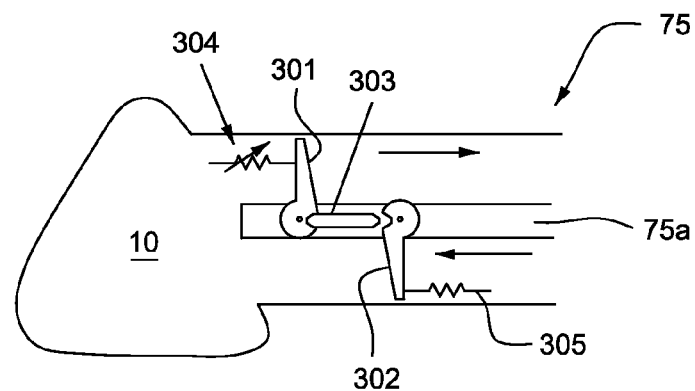
FIG. 50 depicts a mask system having interconnected inlet and exhaust valves.

Referring to FIG. 50, the mask 10 may be connected to the tube 75 which includes an interconnected exhaust valve 301 and inlet valve 302. The exhaust valve 301 and inlet valve 302 are connected by a sliding interlock 303 that is slidably supported by a partition 75*a* in the tube 75. The partition 75*a* divides the tube 75 so that the pressurised flow of breathable gas may be delivered to the mask from the flow generator and the patient's exhalation may be exhausted in the same tube 75. The exhaust valve 301 and the inlet valve 302 may be controlled by adjustable springs 304 and 305, respectively.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. Furthermore, each individual component of any given assembly, one or more portions of an individual component of any given assembly, and various combinations of components from one or more embodiments may include one or more ornamental design features. In addition, while the invention has particular application to patients who suffer from OSA, it is to be appreciated that patients who suffer from other illnesses (e.g., congestive heart failure, diabetes, morbid obesity, stroke, barriatric surgery, etc.) can derive benefit from the above teachings. Moreover, the above teachings have applicability with patients and non-patients alike in non-medical applications.

What is claimed is:

1. A patient interface for improving patient comfort during CPAP therapy, the patient interface comprising:
   a cushion defining a chamber and adapted to sealingly engage a patient's face; and
   a venting arrangement defining at least a portion of an expiratory flow path and comprising a) an opening in the chamber configured to allow communication between an interior of the patient interface and an exterior of the patient interface and b) a moveable portion configured to adjust the expiratory flow path, the movable portion being arranged to reduce expiratory pressure in the chamber to a level below a predetermined CPAP therapy pressure at a first rate and increase the reduced expiratory pressure in the chamber back up to them CPAP therapy pressure at a second rate, the first rate being greater than the second rate.

2. The patient interface according to claim 1, wherein the venting arrangement comprises a normally closed demand valve that is openable responsive to patient inhalation.

3. The patient interface according to claim 2, wherein the venting arrangement further comprises a normally closed pressure relief valve that is openable responsive to patient exhalation.

4. The patient interface according to claim 3, wherein the venting arrangement further comprises an interlocking arrangement connecting the demand valve and the pressure relief valve such that only one of the demand valve and the pressure relief valve can be opened at one time.

5. The patient interface according to claim 1, wherein the venting arrangement comprises a piston in the patient interface configured to change a volume of the patient interface during patient inhalation and expiration.

6. The patient interface according to claim 1, wherein the venting arrangement comprises a plurality of vents in the patient interface, wherein each vent is openable at a different expiratory pressure.

7. The patient interface according to claim 1, wherein the venting arrangement comprises a flow diverter in a tube configured to deliver a flow of pressurised breathable gas, and the flow diverter is configured to divert flow away from the patient interface during patient expiration.

8. The patient interface according to claim 1, wherein the venting arrangement comprises a vent having openings of variable size.

9. The patient interface according to claim 1, wherein the venting arrangement comprises a vent having a plurality of openings, and at least some of the openings are closed during patient inhalation and open during patient expiration, or vice versa.

10. The patient interface according to claim 9, wherein the at least some openings are covered by memory material.

11. The patient interface according to claim 10, wherein the memory material is a foam or a memory alloy.

12. The patient interface according to claim 9, wherein the at least some openings are covered by a membrane comprising crosshatched elastic fibres.

13. The patient interface according to claim 9, wherein the at least some openings are covered by a thin, flexible plate.

14. The patient interface according to claim 1, wherein the venting arrangement comprises a variable inlet restriction provided in a tube configured to deliver a pressurised flow of breathable gas or in an inlet of a patient interface connected to the tube and configured to deliver the pressurized flow to the patient.

15. The patient interface according to claim 14, wherein the variable inlet restriction comprises a flexible membrane bladder in the tube or inlet, the flexible membrane bladder being connected to the expiratory flow of the patient to expand during patient expiration and restrict the tube or inlet.

16. The patient interface according to claim 15, wherein the tube or inlet comprises holes to permit the expiratory flow to leak from the flexible membrane bladder during passive patient expiration.

17. The patient interface according to claim 1, wherein the venting arrangement comprises a tube comprising an inner tube for patient inhalation and an outer tube surrounding the inner tube for patient exhalation.

18. The patient interface according to claim 1, wherein the venting arrangement comprises a regulator to alternately open first and second chambers, the first chamber being open during patient inhalation and closed during patient expiration, and the second chamber being closed during patient inhalation and open during patient expiration.

19. The patient interface according to claim 1, wherein the venting arrangement includes a demand valve configured to provide a constant leak of a pressurised flow of breathable gas.

20. The patient interface according to claim 19, wherein the demand valve comprises a diaphragm as a sensing element.

21. The patient interface according to claim 19, wherein the venting arrangement further comprises a one way vent.

22. The patient interface according to claim 1, wherein the venting arrangement comprises a first one-way valve and a second one-way valve.

23. The patient interface according to claim 22, wherein the first and second one-way valves are configured to provide a small leak of a pressurised flow of breathable gas.

24. The patient interface according to claim 22, wherein the first one-way valve is open and the second one-way valve is closed during patient inhalation.

25. The patient interface according to claim 22, wherein the first one-way valve is closed and the second one-way valve is open during patient exhalation.

26. The patient interface according to claim 22, wherein a loading element of the one-way valves comprises a spring.

27. The patient interface according to claim 26, wherein the spring comprises a compression spring.

28. The patient interface according to claim 26, wherein the spring comprises a tension spring.

29. The patient interface according to claim 26, further comprising an adjustment mechanism to adjust a force of the spring.

30. The patient interface according to claim 29, wherein the adjustment mechanism comprises a knob.

31. The patient interface according to claim 22, wherein a sensing element of at least one of the one-way valves comprises a taper.

32. The patient interface according to claim 1, wherein the venting arrangement comprises a positive end expiratory pressure valve that provides a constant leak of a pressurised flow of breathable gas.

33. A CPAP system configured to provide CPAP therapy to a patient, the CPAP system comprising:
    a flow generator configured to generate a flow of pressurised breathable gas;

a patient interface according to claim 1; and a tube configured to connect the patient interface to the flow generator.

34. The patient interface according to claim 1, wherein the venting arrangement is arranged to provide a substantially sinusoidal pressure-time waveform of inspiratory and expiratory pressure.

35. The patient interface according to claim 1, wherein the moveable portion is a flexible plate that is movable with respect to the opening and is biased toward the opening, the flexible plate being adapted to prevent gas from flowing through the opening when the flexible plate is positioned against the opening.

36. The patient interface according to claim 35, wherein the flexible plate is configured to move away from the opening in response to a threshold inspiratory pressure, a velocity of the movement away from the opening being greater than a velocity of a return movement back toward the opening.

37. The patient interface according to claim 36, wherein the venting arrangement further comprises a pre-loaded spring biasing mechanism configured to bias the flexible plate toward the opening.

38. The patient interface according to claim 37, wherein the venting arrangement comprises a plurality of openings and at least some of the openings are closed during patient inhalation and open during patient expiration, or vice versa.

39. The patient interface according to claim 1, wherein the venting arrangement comprises a one-way damper.

40. The patient interface according to claim 1, wherein the venting arrangement is arranged to reduce the expiratory pressure to a predetermined pressure.

41. The patient interface according to claim 1, wherein the predetermined CPAP therapy pressure is great enough to splint a patient's upper airway open during sleep.

42. The patient interface according to claim 1, wherein the venting arrangement is configured to reduce the expiratory pressure during a period of active exhalation and increase the expiratory pressure during a period of passive exhalation.

43. An apparatus comprising the patient interface of claim 1, wherein the patient interface is configured to sealingly deliver of a flow of breathable gas at a continuously positive pressure with respect to ambient air pressure to an entrance of a patient's airways including at least an entrance of the patient's nares, and wherein the apparatus is configured to maintain a therapy pressure in a range of about 4 cm $H_2O$ to about 20 cm $H_2O$ above ambient air pressure throughout the patient's respiratory cycle while the patient is sleeping to ameliorate sleep disordered breathing.

* * * * *

UNITED STATES PATENT AND TRADEMARK OFFICE
CERTIFICATE OF CORRECTION

| | | |
|---|---|---|
| PATENT NO. | : 9,259,547 B2 | Page 1 of 1 |
| APPLICATION NO. | : 12/438871 | |
| DATED | : February 16, 2016 | |
| INVENTOR(S) | : Meynink et al. | |

It is certified that error appears in the above-identified patent and that said Letters Patent is hereby corrected as shown below:

In the claims

In claim 1, at column 21, line 23, "pressure in the chamber back up to them CPAP" should be corrected to "pressure in the chamber back up to the CPAP--".

Signed and Sealed this
Tenth Day of May, 2016

Michelle K. Lee
*Director of the United States Patent and Trademark Office*